(12) United States Patent
Sorori et al.

(10) Patent No.: US 6,322,950 B1
(45) Date of Patent: Nov. 27, 2001

(54) PHOTOSENSITIVE COMPOSITION AND 1,3-DIHYDRO-1-OXO-2H-INDENE DERIVATIVE

(75) Inventors: Tadahiro Sorori; Yasubumi Murota; Koichi Kawamura; Kazuto Kunita, all of Shizuoka (JP)

(73) Assignee: Fuji Photo Film Co., Ltd., Minami-Ashigara (JP)

( * ) Notice: Subject to any disclaimer, the term of this patent is extended or adjusted under 35 U.S.C. 154(b) by 0 days.

(21) Appl. No.: 09/520,839

(22) Filed: Mar. 8, 2000

(30) Foreign Application Priority Data

Mar. 9, 1999 (JP) .................................................. 11-061559

(51) Int. Cl.⁷ .................................................... G03F 7/027
(52) U.S. Cl. .................................. 430/281.1; 430/288.1; 430/926; 522/31; 522/60; 522/63; 522/75
(58) Field of Search ............................... 430/270.1, 281.1, 430/288.1, 926; 549/32; 548/152; 522/31, 60, 63, 75

(56) References Cited

U.S. PATENT DOCUMENTS 5,202,221 * 4/1993 Imai et al. ........................... 430/283
5,807,659 * 9/1998 Nishimiya et al. ................... 430/302
5,837,748 * 11/1998 Sorori et al. .......................... 522/26

OTHER PUBLICATIONS

"1,3–Dithiol–2–ylidene Derivatives of 1,3–Indanedione", M.R. Bryce et al., Tetrahedron, 55, 1999, 9915–9922.*

CA60:8162g abstract.*

* cited by examiner

Primary Examiner—Rosemary Ashton
(74) Attorney, Agent, or Firm—Burns, Doane, Swecker & Mathis, LLP

(57) ABSTRACT

A photosensitive composition for short wave exposure use, which comprises (i) a sensitizing dye as a 1,3-dihydro-1-oxo-2H-indene derivative having a specified structure, (ii) an activator compound that generates chemical changes by its interaction with an electronic excitation condition induced by light absorption of the sensitizing dye represented by formula (I) and thereby produces at least any one of radicals, acids and bases and (iii) a compound whose physical or chemical characteristics are changed and maintained by undergoing reaction with at least one of radicals, acids and bases.

6 Claims, No Drawings

PHOTOSENSITIVE COMPOSITION AND 1,3-DIHYDRO-1-OXO-2H-INDENE DERIVATIVE

FIELD OF THE INVENTION

This invention relates to a photosensitive composition which contains a novel photo-initiation system, particularly a photo-initiation system having high sensitivity and excellent stability. This invention also relates to a photopolymerizable composition which is particularly excellent as a material for use in the lithographic printing plate precursors, by which plate making can be effected by the scanning exposure based on digital signals.

BACKGROUND OF THE INVENTION

In the prior art, PS plates having a construction in which a lipophilic photosensitive resin layer is provided on a hydrophilic support have been broadly used as lithographic printing plates, and desired printing plates have been obtained generally a plate making method in which a masking exposure (surface exposure) is carried out via a lith film and then non-image parts are dissolved and removed.

In recent years, digitalization techniques in which image information is electronically treated, accumulated and output using a computer have been widely popularized, and various corresponding new image output systems have been put into practical use. As a result, there is a demand for a computer to plate (CTP) technique for directly producing a printing plate without mediating a lith film by scanning a high directivity light such as laser beam according to the digitized image information, and production of the printing plate precursors suited for such a technique therefore is now an important technical subject.

As one of the methods for obtaining such lithographic printing plates capable of effecting scanning exposure, a construction in which a photopolymerization system composition having excellent sensitizing speed is used as an ink-acceptable photosensitive resin layer (to be referred to as "photosensitive layer" hereinafter) to be provided on a hydrophilic support has been proposed and is already on the market. A precursor of such a construction renders possible simple and easy developing treatment and has desirable machine plate making and printing properties such as excellent resolution, inking property, printing durability and anti-scumming property.

The aforementioned photopolymerizable composition basically comprises an ethylenic unsaturated compound, a photopolymerization initiation system and a binder resin, and the image formation is effected by a process in which the photo-initiation system absorbs light to form an active radical which induces addition polymerization of the ethylenic unsaturated compound to cause insolubilization of the photosensitive layer. Most of the prior art proposals regarding photopolymerizable compositions capable of effecting scanning exposure disclose the use of photo-initiation systems having excellent photosensitivity and are described for example by Bruce M. Monroe et al. in *Chemical Review*, 93, 435 (1993) and by R. S. Davidson in *Journal of Photochemistry and Biology A: Chemistry*, 73, 81 (1993).

Regarding the background art CTP system which uses a photopolymerizable composition comprising such an initiation system and a long wavelength visible light source such as Ar laser (488 nm) or FD-YAG laser (532 nm) as the light source, writing at a more higher speed is expected for the purpose of improving productivity of the plate making step, but such a purpose has not been achieved yet because of insufficient output of the light source and insufficient sensitivity of the photosensitive material.

On the other hand, a semiconductor laser which uses, for example, an InGaN system material and can effect continuous oscillation at a range of from 350 nm to 450 nm has been put into practical steps in recent years. In the scanning exposure system which uses these short wavelength light sources, the semiconductor laser can be produced with low cost due to its structure, so that it is possessed of an advantage in that an economical system having sufficient output can be constructed. In addition, in comparison with the prior art system which uses FD-YAG or Ar laser, it renders possible the use of a photosensitive material which has a short wavelength photosensitive range and can be handled under a brighter safe light.

However, no information is available to date concerning a photo-initiation system having sufficient sensitivity for scanning exposure at a short wavelength region of from 350 nm to 450 nm.

In addition, as is described for example by J. P. Faussier in "Photoinitiated Polymerization—Theory and Applications": *Rapra Review* vol. 9, *Report, Rapra Technology* (1998) and by M. Tsunooka et al. in *Prog. Polym. Sci.*, 21, 1 (1996), construction of a photoinitiation system having high sensitivity is a technique still greatly expected in the imaging field. Since a photoinitiation system comprising a sensitizing dye and an activator can generate an acid or base in addition to the aforementioned active radical, by selecting the activator, it is used for example in the image formation such as optical image formation, holography or color hard copy, in the field of electronic material production such as of photo resists and in photo-curing resin materials such as ink, paints and adhesives. In these industrial fields, there is a demand for finding a sensitizing dye having excellent light absorption ability and sensitizing ability, in order to induce decomposition of the activator efficiently.

SUMMARY OF THE INVENTION

The object of the present invention is to provide a photosensitive composition which uses a novel photo-initiation system having high sensitivity for a wide wavelength region of from 350 nm to 450 nm and is suited for lithographic printing plate precursors having high sensitivity for the oscillation wavelength of inexpensive short wave semiconductor lasers, for the purpose of obtaining a lithographic printing plate for scanning exposure use which is excellent in terms of workability and economy and suited for the CTP system.

Another object of the present invention is to provide a novel compound which can be used in the composition.

With the aim of achieving the above objects, the inventors of the present invention have conducted intensive studies and found as a result of the efforts that a novel photo-initiation system comprising a sensitizing dye having a specified structure and an activator compound can give particularly high photosensitive property.

Specifically, it was found that a photo-initiation system which comprises (i) a sensitizing dye represented by formula (I) and (ii) an activator compound that generates chemical changes by its interaction with an electronic excitation condition induced by light absorption of the sensitizing dye represented by the formula (I), thereby producing at least any one of radicals, acids and bases, has markedly high photosensitivity and shows high sensitivity particularly at a wavelength of approximately from 350 to 450 nm.

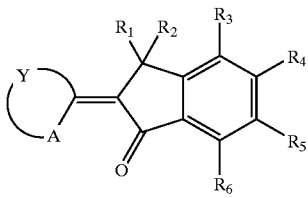

(I)

wherein A represents S atom or $NR_7$, Y represents a non-metallic atomic group which forms a basic nucleus of the pigment together with the adjacent A and carbon atom, each of $R_1$, $R_2$, $R_3$, $R_4$, $R_5$ and $R_6$ independently represents a monovalent group of the non-metallic atomic group, and $R_7$ represents an alkyl group or an aryl group.

The above-described initiation system can provide an excellent photosensitive composition in combination with (iii) a compound whose physical or chemical characteristics are changed and maintained by undergoing reaction with at least one of radicals, acids and bases.

It was found also that a lithographic printing plate precursor which has sufficient sensitivity for scanning exposure by a short wave semiconductor laser, can be handled under a bright safe light and shows excellent printing ability can be obtained by the use of the photosensitive composition in which the compound (iii) whose physical or chemical characteristics are changed and maintained by undergoing reaction with at least any one of radicals, acids and bases is an addition-polymerizable compound having an ethylenic unsaturated double bond.

Also, in order to obtain the effects of the present invention, it is desirable that the sensitizing dye (i) represented by the formula (I) is a 1,3-dihydro-1-oxo-2H-indene derivative represented by formula (II), and this compound is a novel compound.

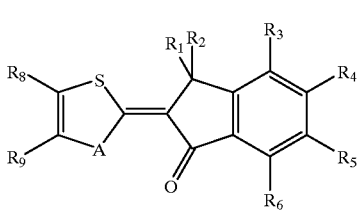

(II)

wherein A represents S atom or $NR_7$, each of $R_1$, $R_2$, $R_3$, $R_4$, $R_5$, $R_6$, $R_8$ and $R_9$ independently represents a monovalent group of the non-metallic atomic group, and $R_7$ represents an alkyl group or an aryl group, wherein $R_8$ and $R_9$ may combine with each other to form a five- to eight-membered ring.

DETAILED DESCRIPTION OF THE INVENTION

Embodiment of the present invention is described in detail below.

A. Photo-initiation system

The photo-initiation system of the present invention comprises (i) a sensitizing dye 1,3-dihydro-1-oxo-2H-indene derivative having a specified structure and (ii) an activator compound which generates chemical changes by its interaction with an electronic excitation condition induced by light absorption of the sensitizing dye and thereby produces at least any one of radicals, acids and bases.

One of the characteristics of the sensitizing dye (i) of the present invention is that it shows particularly excellent absorption property at a wavelength region of from 350 nm to 450 nm. In addition, the dye (i) shows markedly high photosensitivity by efficiently inducing decomposition of various activators. As the sensitization mechanism of a photo-initiation system comprising a sensitizing dye and an activator, some pathways are generally known, such as (1) reductive decomposition of the activator, based on the electron transfer from the electronic excitation condition of the sensitizing dye to the activator, (2) oxidative decomposition of the activator, based on the electron transfer from the activator to the electronic excitation condition of the sensitizing dye and (3) decomposition of the activator from its electronic excitation condition, based on the energy transfer from the electronic excitation condition of the sensitizing dye to the activator, and it was found that the sensitizing dye of the present invention can induce any type of these sensitization reactions with excellent efficiency.

The present inventors have found that the presence of a 1,3-dihydro-1-oxo-2H-inden-2-yl partial structure in the sensitizing dye is markedly important for obtaining high sensitivity, though its action mechanism is not clear yet. The sensitizing dye of the present invention shows high strength emission (fluorescence and/or phosphorescence) spectrum. Thus, it can be considered as one of the possibilities that the sensitizing dye of the present invention having the above-described partial structure has a relatively long life of its excitation condition which therefore contributes to the improved efficiency of its reaction with the activator. Another possibility is that the 1,3-dihydro-1-oxo-2H-inden-2-yl partial structure is contributing to the improved efficiency of a sensitization reaction initial step (e.g., electron transfer) and further to the improved efficiency of subsequent reactions until decomposition of the activator.

(A1) Sensitizing dye

The sensitizing dye to be used in the present invention is a compound represented by the following formula (I).

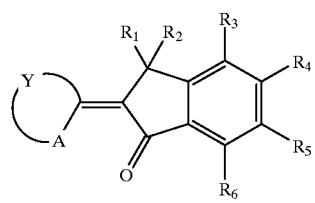

(I)

In the formula (I), A represents S atom or $NR_7$, Y represents a non-metallic atomic group which forms basic nucleus of the dye together with the adjacent A and carbon atom, each of $R_1$, $R_2$, $R_3$, $R_4$, $R_5$ and $R_6$ independently represents a monovalent group of the non-metallic atomic group, and $R_7$ represents an alkyl or aryl group.

The formula (I) described in detail. A is S atom or $NR_7$, $R_7$ is a substituted or unsubstituted alkyl group or a substituted or unsubstituted aryl group and Y is a non-metallic atomic group which forms basic nucleus of the dye together with the adjacent A and adjacent carbon atom.

Preferred examples of the $R_7$ are illustratively described. Linear, branched and cyclic alkyl groups having from 1 to 20 carbon atoms can be cited as preferred examples of the alkyl group, and specific examples thereof include methyl group, ethyl group, propyl group, butyl group, pentyl group, hexyl group, heptyl group, octyl group, nonyl group, decyl group, undecyl group, dodecyl group, tridecyl group, hexadecyl group, octadecyl group, eicosyl group, isopropyl group, isobutyl group, s-butyl group, t-butyl group, isopentyl group, neopentyl group, 1-methylbutyl group, isohexyl group, 2-ethylhexyl group, 2-methylhexyl group, cyclohexyl group, cyclopentyl group and 2-norbornyl group. More preferred among these alkyl groups are a linear group having from 1 to 12 carbon atoms, a branched group having from 3 to 12 carbon atoms and a cyclic group having from 5 to 10 carbon atoms.

Regarding the substituent group of the substituted alkyl group, a group of monovalent non-metallic atomic groups excluding hydrogen is used, and its preferred examples include a halogen atom (—F, —Br, —Cl or —I), hydroxyl group, an alkoxy group, an aryloxy group, a mercapto group, an alkylthio group, an arylthio group, an alkyldithio group, an aryldithio group, amino group, an N-alkylamino group, an N,N-dialkylamino group, an N-arylamino group, an N,N-diarylamino group, an N-alkyl-N-arylamino group, an acyloxy group, a carbamoyloxy group, an N-alkylcarbamoyloxy group, an N-arylcarbamoyloxy group, an N,N-dialkylcarbamoyloxy group, an N,N-diarylcarbamoyloxy group, an N-alkyl-N-arylcarbamoyloxy group, an alkylsulfoxy group, an arylsulfoxy group, an acyloxy group, an acylthio group, an acylamino group, an N-alkylacylamino group, an N-arylacylamino group, a ureido group, an N'-alkylureido group, an N',N'-dialkylureido group, an N'-arylureido group, an N',N'-diarylureido group, an N'-alkyl-N'-arylureido group, an N-alkylureido group, an N-arylureido group, an N'-alkyl-N-alkylureido group, an N'-alkyl-N-arylureido group, an N',N'-dialkyl-N-alkylureido group, an N',N'-dialkyl-N-arylureido group, an N'-aryl-N-alkylureido group, an N'-aryl-N-arylureido group, an N',N'-diaryl-N-alkylureido group, an N',N'-diaryl-N-arylureido group, an N'-alkyl-N'-aryl-N-alkylureido group, an N'-alkyl-N'-aryl-N-arylureido group, an alkoxycarbonylamino group, an aryloxycarbonylamino group, an N-alkyl-N-alkoxycarbonylamino group, an N-alkyl-N-aryloxycarbonylamino group, an N-aryl-N-alkoxycarbonylamino group, an N-aryl-N-aryloxycarbonylamino group, a formyl group, an acyl group, carboxyl group, an alkoxycarbonyl group, an aryloxycarbonyl group, carbamoyl group, an N-alkylcarbamoyl group, an N,N-dialkylcarbamoyl group, an N-arylcarbamoyl group, an N,N-diarylcarbamoyl group, an N-alkyl-N-arylcarbamoyl group, an alkylsulfinyl group, an arylsulfinyl group, an alkylsulfonyl group, an arylsulfonyl group, sulfo group (—$SO_3H$) and its conjugate base group (to be referred to as sulfonato group hereinafter), an alkoxysulfonyl group, an aryloxysulfonyl group, a sulfinamoyl group, an N-alkylsulfinamoyl group, an N,N-dialkylsulfinamoyl group, an N-arylsulfinamoyl group, an N,N-diarylsulfinamoyl group, an N-alkyl-N-arylsulfinamoyl group, a sulfamoyl group, an N-alkylsulfamoyl group, an N,N-dialkylsulfamoyl group, an N-arylsulfamoyl group, an N,N-diarylsulfamoyl group, an N-alkyl-N-arylsulfamoyl group, phosphono group (—$PO_3H_2$) and its conjugate base group (to be referred to as phosphonato group hereinafter), a dialkylphosphono group (—$PO_3(alkyl)_2$), a diarylphosphono group (—$PO_3(aryl)_2$), an alkylarylphosphono group (—$PO_3(alkyl)(aryl)$) group, a monoalkylphosphono group (—$PO_3H(alkyl)$) and its conjugate base group (to be referred to as alkylphosphonato group hereinafter), a monoarylphosphono group (—$PO_3H(aryl)$) and its conjugate base group (to be referred to as arylphosphonato group hereinafter), phosphonooxy group (—$OPO_3H_2$) and its conjugate base group (to be referred to as phosphonatooxy group hereinafter), a dialkylphosphonooxy group (—$OPO_3(alkyl)_2$), a diarylphosphonooxy group (—$OPO_3(aryl)_2$), an alkylarylphosphonooxy group (—$OPO_3(alkyl)(aryl)$) group, a monoalkylphosphonooxy group (—$OPO_3H(alkyl)$) and its conjugate base group (to be referred to as alkylphosphonatooxy group hereinafter), a monoarylphosphonooxy group (—$OPO_3H(aryl)$) and its conjugate base group (to be referred to as arylphosphonatooxy group hereinafter), cyano group, nitro group, an aryl group, a heteroaryl group, an alkenyl group, an alkynyl group and silyl group.

Specific examples of the alkyl group in these substituent groups are as described in the foregoing, which may have additional substituent groups, and specific examples of the aryl group include phenyl group, biphenyl group, naphthyl group, tolyl group, xylyl group, mesityl group, cumenyl group, chlorophenyl group, bromophenyl group, chloromethylphenyl group, hydroxyphenyl group, methoxyphenyl group, ethoxyphenyl group, phenoxyphenyl group, acetoxyphenyl group, benzoyloxyphenyl group, methylthiophenyl group, phenylthiophenyl group, methylaminophenyl group, dimethylaminophenyl group, acetylaminophenyl group, carboxyphenyl group, methoxycarbonylphenyl group, ethoxyphenylcarbonyl group, phenoxycarbonylphenyl group, N-phenylcarbamoylphenyl group, phenyl group, cyanophenyl group, sulfophenyl group, sulfonatophenyl group, phosphonophenyl group and phosphonatophenyl group.

Regarding the heteroaryl group, a group derived from a monocyclic or polycyclic aromatic ring containing at least one of nitrogen, oxygen and sulfur atoms is used, and examples of the heteroaryl ring in particularly preferred heteroaryl groups include thiophene, thiathrene, furan, pyran, isobenzofuran, chromene, xanthene, phenoxazine, pyrrole, pyrazole, isothiazole, isoxazole, pyrazine, pyrimidine, pyridazine, indolizine, isoindolizine, indolyl, indazole, purine, quinolizine, isoquinoline, phthalazine, naphthyridine, quinazoline, cinnoline, pteridine, carbazole, carboline, phenanthrene, acridine, perimidine, phenanthroline, phthalazine, phenarsazine, phenoxazine, furazane and phenoxazine, which may be benzo-condensed or have a substituent group.

Examples of the alkenyl group include vinyl group, 1-propenyl group, 1-butenyl group, cinnamyl group and 2-chloro-1-ethenyl group, and examples of the alkynyl group include ethynyl group, 1-propynyl group, 1-butynyl group and trimethylsilylethynyl group. Examples of $G_1$ in the acyl group ($G_1CO$—) include hydrogen and the aforementioned alkyl and aryl groups. Among these substituent groups, more preferred examples include a halogen atom (—F, —Br, —Cl or —I), an alkoxy group, an aryloxy group, an alkylthio group, an arylthio group, an N-alkylamino group, an N,N-dialkylamino group, an acyloxy group, an N-alkylcarbamoyloxy group, an N-arylcarbamoyloxy group, an acylamino group, formyl group, an acyl group, carboxyl group, an alkoxycarbonyl group, an aryloxycarbonyl group, carbamoyl group, an N-alkylcarbamoyl group, an N,N-dialkylcarbamoyl group, an N-arylcarbamoyl group, an N-alkyl-N-arylcarbamoyl group, sulfo group, sulfonato group, sulfamoyl group, an N-alkylsulfamoyl group, an N,N-dialkylsulfamoyl group, an N-arylsulfamoyl group, an N-alkyl-N-arylsulfamoyl group, phosphono group, a phosphonato group, a dialkylphosphono group, a diarylphosphono group, a monoalkylphosphono group, an alkylphosphonato group, a monoarylphosphono group, arylphosphonato group, a phosphonooxy group, a phosphonatooxy group, an aryl group, an alkenyl group and an alkylidene group (e.g., methylene group).

On the other hand, examples of the alkylene group in the substituted alkyl groups include those in which the aforementioned alkyl groups having from 1 to 20 carbon atoms are made into divalent organic residues by removing any one of the hydrogen atoms from each alkyl group, and their preferred examples include linear, branched and cyclic alkylene groups, respectively having from 1 to 12 carbon atoms, from 3 to 12 carbon atoms and from 5 to 10 carbon atoms.

Specific examples of the substituted alkyl group desirable as $R_7$ obtained by the combination of the aforementioned substituent group with alkylene group include chloromethyl group, bromomethyl group, 2-chloroethyl group, trifluoromethyl group, methoxymethyl group, methoxyethoxyethyl group, allyloxymethyl group, phenoxymethyl group, methylthiomethyl group, tritylthiomethyl group, ethylaminoethyl group, diethylaminopropyl group, morpholinopropyl group, acetyloxymethyl group, benzoyloxymethyl group, N-cyclohexylcarbamoyloxyethyl group, N-phenylcarbamoyloxyethyl group, acetylaminoethyl group, N-methylbenzoylaminopropyl group, 2-oxoethyl group, 2-oxopropyl group, carboxypropyl group, methoxycarbonylethyl group, allyloxycarbonylbutyl group, chlorophenoxycarbonylmethyl group, carbamoylmethyl group, N-methylcarbamoylethyl group, N,N-dipropylcarbamoylmethyl group, N-(methoxyphenyl)carbamoylethyl group, N-methyl-N-(sulfophenyl)carbamoylmethyl group, sulfobutyl group, sulfonatopropyl group, sulfonatobutyl group, sulfamoylbutyl group, N-ethylsulfamoylmethyl group, N,N-dipropylsulfamoylpropyl group, N-tolylsulfamoylpropyl group, N-methyl-N-(phosphonophenyl)sulfamoyloctyl group, phosphonobutyl group, phosphanatohexyl group, diethylphosphonobutyl group, diphenylphosphonopropyl group, methylphosphonobutyl group, methylphosphonatobutyl group, tolylphosphonohexyl group, tolylphosphanatohexyl group, phosohonooxypropyl group, phosphonatooxybutyl group, benzyl group, phenethyl group, α-methylbenzyl group, 1-methyl-1-phenylethyl group, p-methylbenzyl group, cinnamyl group, allyl group, 1-propenylmethyl group, 2-butenyl group, 2-methylallyl group, 2-methylpropenylmethyl group, 2-propynyl group, 2-butinyl group and 3-butinyl group.

Illustrative examples of the aryl group desirable as $R_7$ include those in which 1 to 3 benzene rings formed a condensed ring, and benzene ring and a five-membered unsaturated ring formed a condensed ring, such as phenyl group, naphthyl group, anthryl group, phenanthryl group, indenyl group, acenaphthenyl group and fluorenyl group, of which phenyl group and naphthyl group are more desirable.

Illustrative examples of the substituted aryl group desirable as R7 include those in which a group of monovalent non-metallic atomic groups excluding hydrogen is used as a substituent group on the ring-forming carbon atom of the aforementioned aryl groups. Preferred examples of the substituent group include the aforementioned alkyl groups and substituted alkyl groups and the groups cited in the foregoing as the substituent groups in the substituted alkyl groups. Preferred illustrative examples of the substituted aryl group include biphenyl group, tolyl group, xylyl group, mesityl group, cumenyl group, chlorophenyl group, bromophenyl group, fluorophenyl group, chloromethylphenyl group, trifluoromethylphenyl group, hydroxyphenyl group, methoxyphenyl group, methoxyethoxyphenyl group, allyloxyphenyl group, phenoxyphenyl group, methylthiophenyl group, tritylthiophenyl group, ethylaminophenyl group, diethylaminophenyl group, morpholinophenyl group, acetyloxyphenyl group, benzoyloxyphenyl group, N-cyclohexylcarbamoyloxyphenyl group, N-phenylcarbamoyloxyphenyl group, acetylaminophenyl group, N-methylbenzoylaminophenyl group, carboxyphenyl group, methoxycarbonylphenyl group, allyloxycarbonylphenyl group, chlorophenoxycarbonylphenyl group, carbamoylphenyl group, N-methylcarbamoylphenyl group, N,N-dipropylcarbamoylphenyl group, N-(methoxyphenyl)carbamoylphenyl group, N-methyl-N-(sulfophenyl)carbamoylphenyl group, sulfophenyl group, sulfonatophenyl group, sulfamoylphenyl group, N-ethylsulfamoylphenyl group, N,N-dipropylsulfamoylphenyl group, N-tolylsulfamoylphenyl group, N-methyl-N-(phosphonophenyl)sulfamoylphenyl group, phosphonophenyl group, phosphanatophenyl group, diethylphosphonophenyl group, diphenylphosphonophenyl group, methylphosphonophenyl group, methylphosphonatophenyl group, tolylphosphonophenyl group, tolylphosphonatophenyl group, allylphenyl group, 1-propenylmethylphenyl group, 2-butenylphenyl group, 2-methylallylphenyl group, 2-methylpropenylphenyl group, 2-propynylphenyl group, 2-butynylphenyl group and 3-butynylphenyl group.

Next, Y in the formula (I) is described. Y is a non-metallic atomic group which is necessary to form a heterocyclic ring together with the aforementioned A and the adjacent carbon atom. Examples of such a heterocyclic ring include five-, six- or seven-membered nitrogen-containing or sulfur-containing heterocyclic rings which may have a condensed ring, preferably a five- or six-membered heterocyclic ring.

Regarding the nitrogen-containing heterocyclic ring, any one of those which are known to form basic nuclei in merocyanine dyes described for example by L. G. Brooker et al. in *J. Am. Chem. Soc.*, 73, 5326–5358 (1951) and in other references canbeusedpreferably. Its illustrative examples include thiazoles (e.g., thiazole, 4-methylthiazole, 4-phenylthiazole, 5-methylthiazole, 5-phenylthiazole, 4,5-dimethylthiazole, 4,5-diphenylthiazole, 4,5-di(p-methoxyphenylthiazole), 4-(2-thienyl) and 4,5-di(2-furyl) thiazole), benzothiazoles (e.g., benzothiazole, 4-chlorobenzothiazole, 5-chlorobenzothiazole, 6-chlorobenzothiazole, 7-chlorobenzothiazole, 4-methylbenzothiazole, 5-methylbenzothiazole, 6-methylbenzothiazole, 5-bromobenzothiazole, 4-phenylbenzothiazole, 5-phenylbenzothiazole, 4-methoxybenzothiazole, 5-methoxybenzothiazole, 6-methoxybenzothiazole, 5-iodobenzothiazole, 6-iodobenzothiazole, 4-ethoxybenzothiazole, 5-ethoxybenzothiazole, tetrahydrobenzothiazole, 5,6-dimethoxybenzothiazole, 5,6-dioxymethylenebenzothiazole, 5-hydroxybenzothiazole, 6-hydroxybenzothiazole, 6-dimethylaminobenzothiazole and 5-ethoxycarbonylbenzothiazole), naphthothiazoles (e.g., naphtho[1,2]thiazole, naphtho[2,1]thiazole, 5-methoxynaphtho[2,1]thiazole, 5-ethoxynaphtho[2,1]thiazole, 8-methoxynaphtho[1,2]thiazole and 7-methoxynaphtho[1,2]thiazole), thianaphtheno-7',6',4,5-thiazoles (e.g., 4'-methoxythianaphtheno-7',6',4,5-thiazole), oxazoles (e.g., 4-methyloxazole, 5-methyloxazole, 4-phenyloxazole, 4,5-diphenyloxazole, 4-ethyloxazole, 4,5-dimethyloxazole and 5-phenyloxazole), benzoxazoles (e.g., benzoxazole, 5-chlorobenzoxazole, 5-methylbenzoxazole, 5-phenylbenzoxazole, 6-methylbenzoxazole, 5,6-dimethylbenzoxazole, 4,6-dimethylbenzoxazole, 6-methoxybenzoxazole, 5-methoxybenzoxazole, 4-ethoxybenzoxazole, 5-chlorobenzoxazole, 6-methoxybenzoxazole, 5-hydroxybenzoxazole and 6-hydroxybenzoxazole), naphthooxazoles (e.g., naphtho[1,2]oxazole and naphtho[2,1]oxazole), selenazoles (e.g., 4-methylselenazole and 4-phenylselenazole), benzoselenazoles (e.g., benzoselenazole, 5-chlorobenzoselenazole, 5-methoxybenzoselenazole, 5-hydroxybenzoselenazole and tetrahydrobenzoselenazole), naphthoselenazoles (e.g., naphtho[1,2]selenazole and naphtho[2,1]selenazole), thiazolines (e.g., thiazoline, 4-methylthiazoline, 4,5-dimethylthiazoline, 4-phenylthiazoline, 4,5-di(2-furyl) thiazoline, 4,5-diphenylthiazoline and 4,5-di(p-methoxyphenyl)thiazoline), 2-quinolines (e.g., quinoline, 3-methylquinoline, 5-methylquinoline, 7-methylquinoline, 8-methylquinoline, 6-chloroquinoline, 8-chloroquinoline, 6-methoxyquinoline, 6-ethoxyquinoline, 6-hydroxyquinoline and 8-hydroxyquinoline), 4-quinolines (e.g., quinoline, 6-methoxyquinoline, 7-methylquinoline and 8-methylquinoline), 1-isoquinolines (e.g., isoquinoline and 3,4-dihydroisoquinoline), 3-isoquinolines (e.g., quinoline), benzimidazoles (e.g., 1,3-dimethylbenzimidazole, 1,3-diethylbenzimidazole and 1-ethyl-3-phenylbenzimidazole), 3,3-dialkylindolenines (e.g., 3,3-dimethylindolenine, 3,3,5-trimethylindolenine and 3,3,7-trimethylindolenine), 2-pyridines (e.g., pyridine and 5-methylpyridine) and 4-pyridine (e.g., pyridine). In addition, substituent groups of these rings may be linked together to form a ring.

The dithiol partial structures in dyes described in JP-A-3-296759 can be cited as examples of the sulfur-containing heterocyclic ring.

Their illustrative examples include benzodithiols (e.g., benzodithiol, 5-t-butylbenzodithiol and 5-methylbenzodithiol), naphthodithiols (e.g., naphtho[1,2] dithiol and naphtho[2,1]dithiol) and dithiols (e.g., 4,5-dimethyldithiols, 4-phenyldithiols, 4-methoxycarbonyldithiols, 4,5-dimethoxycarbonyldithiols, 4,5-diethoxycarbonyldithiols, 4,5-ditrifluoromethyldithiol, 4,5-dicyanodithiol, 4-methoxycarbonylmethyldithiol and 4-carboxymethyldithiol).

Further, although the above-described examples of the heterocyclic rings are illustrated in terms of heterocyclic ring mother compounds in accordance with the usual manner, these heterocyclic rings are actually represented as dihydro alkylidene substituents to form the partial structure of the dye (I).

Among the aforementioned examples of the nitrogen-containing or sulfur-containing heterocyclic ring formed by the binding of Y to the aforementioned A and the adjacent carbon atom in the formula (I), a dye having the following partial structural formula (I-A) is particularly desirable, because it provides a photopolymerizable composition which not only has high sensitization ability but also is markedly excellent in preservation stability. In the formula (I), the dye having a structure represented by the partial structural in formula (I-A) is a novel compound.

(Partial structural formula)

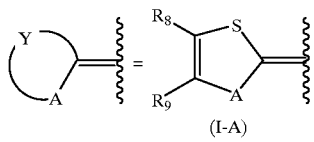

(I-A)

In the formula (I-A), A is as defined in the formula (I) and each of $R_8$ and $R_9$ independently represents a monovalent group of a non-metallic atomic group, wherein $R_8$ and $R_9$ may combine with each other to form a five- to eight-membered ring.

Examples of particularly desirable $R_8$ and $R_9$ include hydrogen atom, a substituted or unsubstituted alkyl group, a substituted or unsubstituted aryl group and a substituted or unsubstituted heteroaryl group. More illustrative examples of these substituent groups are as described in the foregoing as examples of $R_7$. Particularly preferred $R_8$ and $R_9$ are each independently an alkyl group having from 1 to 6 carbon atoms, which may be branched, phenyl group which may have a substituent group, furyl group which may have a substituent group, thienyl group and an alkoxycarbonyl group. When $R_8$ and $R_9$ combine with each other to form a five-, six- or seven-membered ring, their particularly preferred examples are those which form benzene ring or naphthalene ring or constitute trimethylene (—$(CH_2)_3$—) or tetramethylene (—$(CH_2)_4$—).

Next, $R_1$ to $R_6$ in the formula (I) are described in detail.

Regarding $R_1$, $R_2$, $R_3$, $R_4$, $R_5$ and $R_6$, a monovalent group of non-metallic atomic groups can be used each independently, and its more preferred examples include hydrogen atom, a halogen atom, an alkyl group, a substituted alkyl group, an aryl group, a substituted aryl group, an alkenyl group, a substituted alkenyl group, hydroxyl group, a substituted oxy group, mercapto group, a substituted thio group, amino group, a substituted amino group, a substituted carbonyl group, sulfo group, sulfonato group, a substituted sulfinyl group, a substituted sulfonyl group, phosphono group, a substituted phosphono group, phosphonato group, a substituted phosphonato group, cyano group, nitro group and silyl group. Preferred examples of these substituent groups are as described in the foregoing as examples of $R_7$.

In addition, $R_1$ and $R_2$ may together form an aliphatic ring which may form a spiro ring with the ring containing the carbon atom to which they are linked. Examples of preferred aliphatic ring include three-, five-, six-, seven- and eight-membered aliphatic rings, more preferably three-, five- and six-membered aliphatic rings. They may further have substituent groups on their constituting carbon atoms (examples of the substituent groups include those of the substituted alkyl group cited in the foregoing as examples of $R_7$), and a part of the ring-constituting carbon atoms maybe substituted with a hetero zatom (e.g., oxygen atom, sulfur atom or nitrogen atom). Their preferred illustrative examples include those which form cyclopropane ring, cyclopentane ring, cyclohexane ring, cycloheptane ring, cyclooctane ring, cyclo-1,3-dioxapentane ring, cyclopentene ring, cyclohexene ring, cycloheptene ring, cyclooctene ring, cyclo-1,3-dioxapentene ring or cyclo-1,3-dioxahexene ring.

Also, a case in which $R_3$ and $R_4$, $R_4$ and $R_9$ or $R_5$ and $R_6$ together form an aliphatic or aromatic ring can also be used suitably. Examples of preferred aliphatic ring include five-, six-, seven- and eight-membered aliphatic rings, more preferably five- or six-membered aliphatic ring. They may further have substituent groups on their constituting carbon atoms (examples of the substituent groups include those of the substituted alkyl group cited in the foregoing as examples of $R_7$), and a part of the ring-constituting carbon atoms maybe substituted with a hetero atom (e.g., oxygen atom, sulfur atom or nitrogen atom). Their preferred illustrative examples include those which form benzocyclopentene ring, benzocyclohexene ring, benzocycloheptene ring, benzocyclooctene ring, 1,3-benzocyclohexadiene ring, 1,3-dihydro-1,3-dioxaindene ring or Julolidine ring, together with benzene ring containing carbon atoms to which they are linked, as will be shown later in the formula (B). Examples of the case in which they form an aromatic ring include those which form naphthalene ring or anthracene ring, more preferably naphthalene ring, together with benzene ring containing carbon atoms to which they are linked. They may have substituent groups on their constituting carbon atoms (examples of the substituent groups include those of the substituted alkyl group cited in the foregoing as examples of $R_7$).

Among these groups, more preferred examples of $R_1$ and $R_2$ include hydrogen atom, a halogen atom, an alkyl group, a substituted alkyl group, an aryl group, a substituted aryl group, a substituted carbonyl group and a trialkylsilyl group, and more preferred examples of $R_3$ to $R_6$ include hydrogen atom, a halogen atom, an alkyl group, a substituted alkyl group, an aryl group, a substituted aryl group, hydroxyl group, a substituted oxy group, mercapto group, a substituted thio group, amino group, a substituted amino group and a substituted carbonyl group.

Examples of the partial structure (B) having preferred $R_1$ to $R_6$ are illustratively shown in the following.

Partial structure (B)

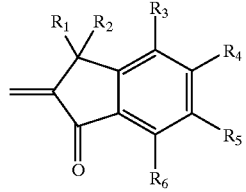

| | $R_1$ | $R_2$ | $R_3$ | $R_4$ | $R_5$ | $R_6$ |
|---|---|---|---|---|---|---|
| (b-1) | —H | —H | —H | —H | —H | —H |
| (b-2) | —CH$_3$ | —H | —H | —H | —H | —H |
| (b-3) | —CH$_3$ | —CH$_3$ | —H | —H | —H | —H |
| (b-4) | —Ph | —H | —H | —H | —H | —H |
| (b-5) | —Ph | —H | —H | —H | —OCH$_3$ | —H |
| (b-6) | —Ph | —H | —H | —OCH$_3$ | —OCH$_3$ | —H |
| (b-7) | —Ph | —H | —H | —OCH$_3$ | —OCH$_3$ | —OCH$_3$ |
| (b-8) | —Ph | —H | —OCH$_3$ | —H | —H | OCH$_3$ |
| (b-9) | —Ph | —H | —CH$_3$ | —H | —H | —CH$_3$ |
| (b-10) | —C$_6$H$_4$-CF$_3$ | —H | —H | —H | —H | —H |
| (b-11) | —C$_6$H$_4$-F | —H | —H | —H | —H | —H |
| (b-12) | —C$_6$H$_4$-Cl | —H | —H | —H | —H | —H |
| (b-13) | —C$_6$H$_4$-OCH$_3$ | —H | —H | —H | —H | —H |
| (b-14) | —C$_6$H$_4$-N(CH$_3$)$_2$ | —H | —H | —H | —H | —H |
| (b-15) | —C$_6$H$_3$(OCH$_3$)$_2$ | —H | —H | —H | —H | —H |
| (b-16) | —Cl | —Cl | —H | —H | —H | —H |
| (b-17) | —C(CH$_3$)$_3$ | —H | —H | —H | —H | —H |
| (b-18) | —CH(CH$_3$)$_2$ | —H | —CH$_3$ | —H | —H | —H |
| (b-19) | —Si(CH$_3$)$_3$ | —H | —CH$_3$ | —H | —H | —H |
| (b-20) | —Si(CH$_3$)$_3$ | —H | —H | —CH$_3$ | —H | —H |
| (b-21) | —Si(CH$_3$)$_3$ | —H | —H | —H | —CH$_3$ | —H |
| (b-22) | —Si(CH$_3$)$_3$ | —H | —H | —H | —H | —CH$_3$ |
| (b-23) | —CH$_3$ | —H | —H | —H | —CH$_3$ | —H |
| (b-24) | —H | —H | —H | —H | —C(CH$_3$)$_3$ | —H |
| (b-25) | —H | —H | —CH$_3$ | —H | —CH(CH$_3$)$_2$ | —H |
| (b-26) | —H | —H | —CH(CH$_3$)$_2$ | —H | —H | —CH$_3$ |
| (b-27) | —CH$_3$ | —CH$_3$ | —H | —C$_2$H$_5$ | —H | —H |

-continued

Partial structure (B)

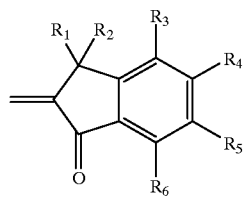

| | $R_1$ | $R_2$ | $R_3$ | $R_4$ | $R_5$ | $R_6$ |
|---|---|---|---|---|---|---|
| (b-28) | —CH$_2$Ph | —H | —H | —CH$_3$ | —H | —H |
| (b-29) | —H | —H | —H | —CH$_3$ | —CH$_3$ | —H |
| (b-30) | —H | —H | —CH$_3$ | —H | —H | —CH$_3$ |
| (b-31) | —Ph | —CH$_3$ | —H | —H | —H | —H |
| (b-32) | —CH$_3$ | —CH$_3$ | —H | —CH$_3$ | —CH$_3$ | —CH$_3$ |
| (b-33) | —CH$_3$ | —CH$_3$ | —CH$_3$ | —CH$_3$ | —H | —CH$_3$ |
| (b-34) | —CH$_3$ | —CH$_3$ | —CH$_3$ | —H | —H | —CH$_3$ |
| (b-35) | —H | —H | —H | —CH$_3$ | —H | —CH$_3$ |
| (b-36) | —H | —H | —CH$_3$ | —H | —H | —CH(CH$_3$)$_2$ |
| (b-37) | —H | —H | —Cl | —H | —H | —H |
| (b-38) | —H | —H | —H | —Cl | —H | —H |
| (b-39) | —H | —H | —H | —H | —Cl | —H |
| (b-40) | —CH$_3$ | —H | —H | —Cl | —H | —H |
| (b-41) | —H | —H | —Cl | —H | —H | —CH$_3$ |
| (b-42) | —H | —H | —CH$_3$ | —H | —H | —Cl |
| (b-43) | —H | —H | —Br | —H | —H | —H |
| (b-44) | —H | —H | —H | —Br | —H | —H |
| (b-45) | —H | —H | —H | —H | —I | —H |
| (b-46) | —H | —H | —CH(CH$_3$)$_2$ | —H | —H | —Br |
| (b-47) | —H | —H | —Br | —H | —H | —CH(CH$_3$)$_2$ |
| (b-48) | —H | —H | —CH$_3$ | —H | —H | —Br |
| (b-49) | —H | —H | —Br | —H | —H | —CH$_3$ |
| (b-50) | —H | —H | —OH | —H | —H | —H |
| (b-51) | —H | —H | —H | —OH | —H | —H |
| (b-52) | —H | —H | —OC$_2$H$_5$ | —H | —H | —H |
| (b-53) | —H | —H | —H | —OCH$_3$ | —H | —H |
| (b-54) | —H | —H | —H | —H | —OCH$_3$ | —H |
| (b-55) | —H | —H | —OCH$_3$ | —OCH$_3$ | —H | —H |
| (b-56) | —H | —H | —H | —OCH$_3$ | —OCH$_3$ | —H |
| (b-57) | —H | —H | —H | —OCH$_3$ | —H | —OCH$_3$ |
| (b-58) | —H | —H | —OCH$_3$ | —OCH$_3$ | —OCH$_3$ | —H |
| (b-59) | —H | —H | —H | —OCH$_3$ | —OCH$_3$ | —OCH$_3$ |
| (b-60) | —H | —H | —OH | —H | —H | —OH |
| (b-61) | —H | —H | —H | —N(CH$_3$)$_2$ | —H | —H |
| (b-62) | —H | —H | —H | —SCH$_3$ | —H | —H |
| (b-63) | —H | —H | —H | —OC$_2$H$_4$CO$_2$H | —H | —H |
| (b-64) | —H | —H | —H | —OC$_2$H$_4$CO$_2$CH$_3$ | —H | —H |
| (b-65) | —H | —H | —H | —H | —CO$_2$H | —H |
| (b-66) | —H | —H | —H | —H | —CO$_2$C$_2$H$_5$ | —H |
| (b-67) | —H | —H | —H | —Ph | —H | —H |
| (b-68) | —H | —H | —NO$_2$ | —H | —H | —H |
| (b-69) | —CH$_3$ | —CH$_3$ | —H | —H | —NO$_2$ | —H |
| (b-70) | —CO$_2$H | —H | —H | —H | —H | —H |
| (b-71) | —CH$_2$CO$_2$H | —H | —H | —H | —H | —H |
| (b-72) | —CO$_2$C$_2$H$_5$ | —H | —H | —H | —H | —H |
| (b-73) | —Si(CH$_3$)$_3$ | —H | —H | —H | —H | —H |
| (b-74) | —SCH$_3$ | —H | —H | —H | —H | —H |
| (b-75) | —H | —H | —H | —H | —H | —OCH$_3$ |
| (b-76) | —H | H | —H | —CCl$_3$ | —H | —H |
| (b-77) | —OCH$_2$CH=CH$_2$ | —H | —H | —H | —H | —H |
| (b-78) | —C$_4$H$_9$ | —H | —H | —H | —H | —H |
| (b-79) | —H | —H | —H | —OCH$_2$CH=CH$_2$ | —H | —H |
| (b-80) | —H | —H | —H | —NHCH$_2$(CO$_2$H) | —H | —H |
| (b-81) | —M | —H | —H | —PO$_3$H | —H | —H |

(b-82)

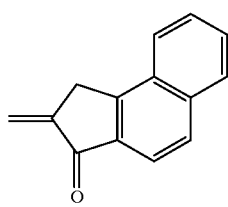

(b-83)

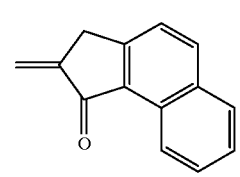

(b-84)

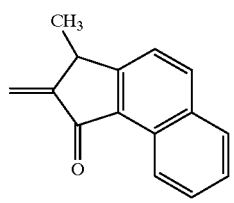

-continued

Partial structure (B)

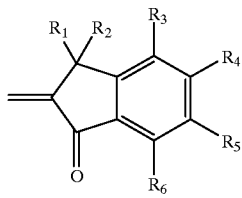

| R₁ | R₂ | R₃ | R₄ | R₅ | R₆ |
|---|---|---|---|---|---|

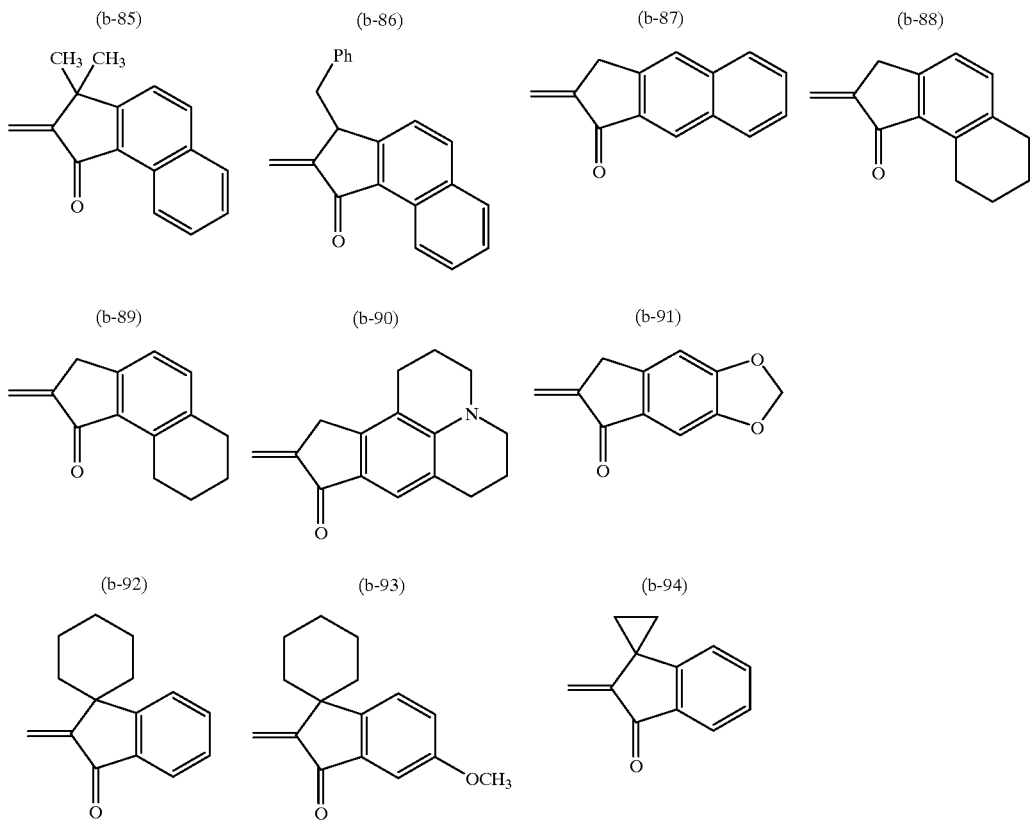

The compound of the formula (I) can be formed by optionally combining a basic nucleus formed by the aforementioned A and Y together with the adjacent carbon atom with a 1,3-dihydro-1-oxo-2H-indenylidene nucleus of the partial structure (B). Preferred illustrative examples (D1) to (D52) of the compound of formula (I) are shown below, though the present invention is not restricted thereby.

(D1)

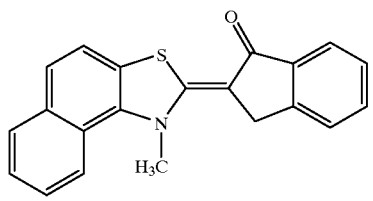

-continued (D2) (D3) (D4) (D5) (D6) (D7) (D8) (D9) (D10) (D11) (D12) (D13) (D14) (D15)

(D16) 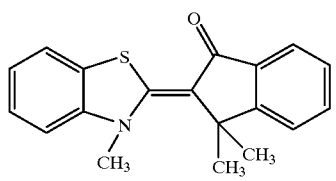
(D17) 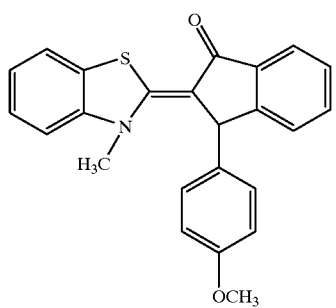
(D18) 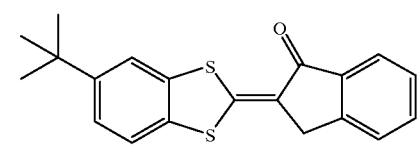
(D19) 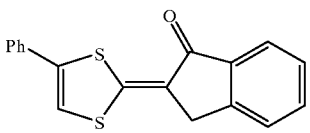
(D20) 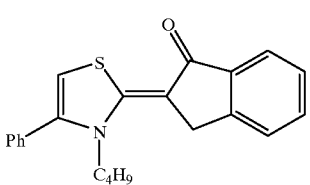
(D21) 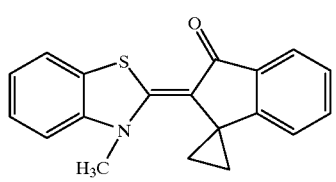
(D22) 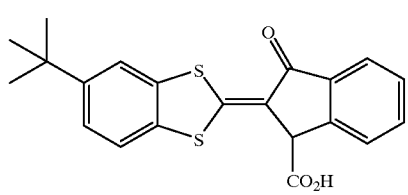
(D23) 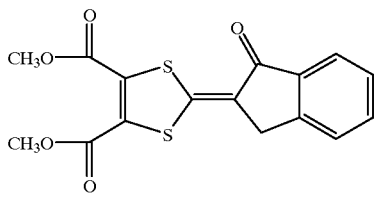
(D24) 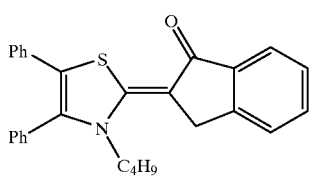
(D25) 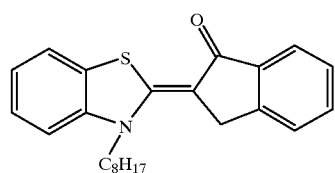
(D26) 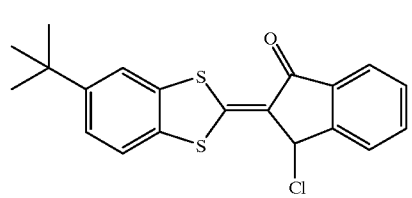
(D27) 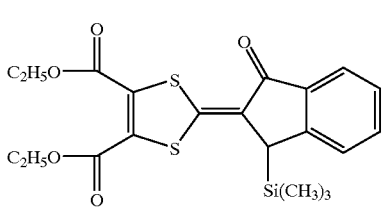
(D28) 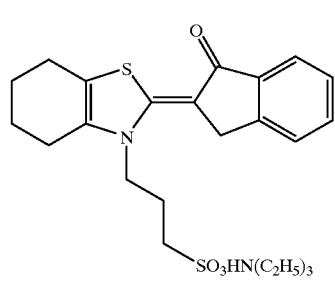
(D29) 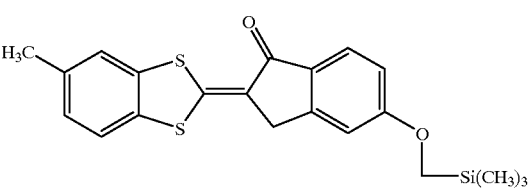

(D30) 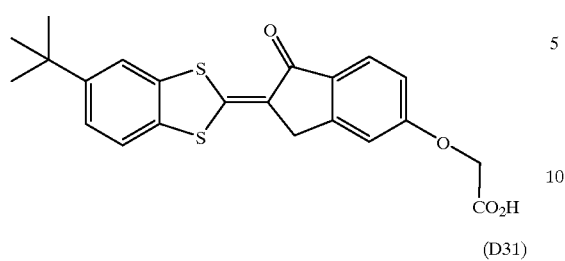
(D31) 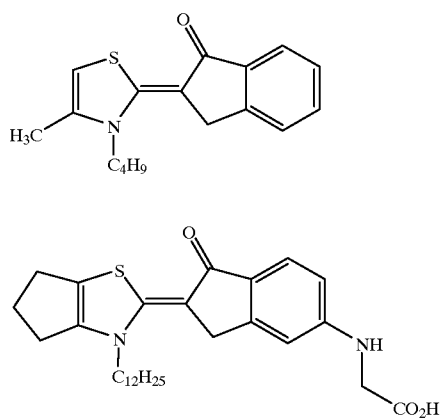
(D32)
(D33) 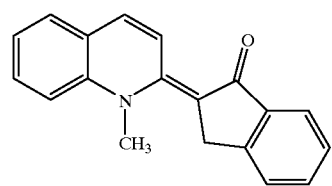
(D34) 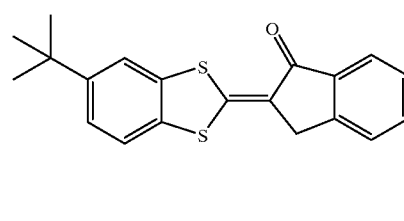
(D35) 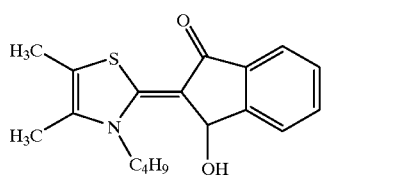
(D36) 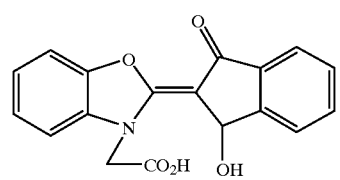
(D37) 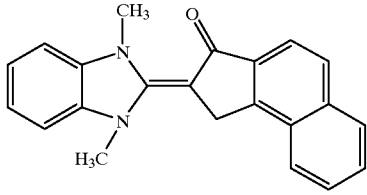
(D38) 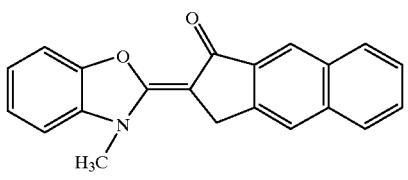
(D39) 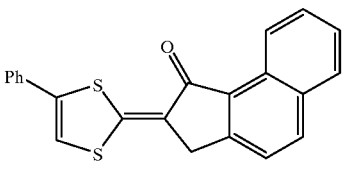
(D40) 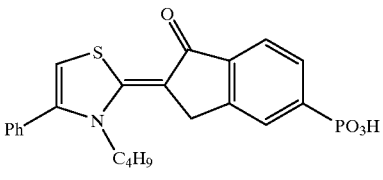
(D41) 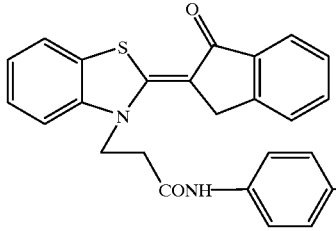
(D42) 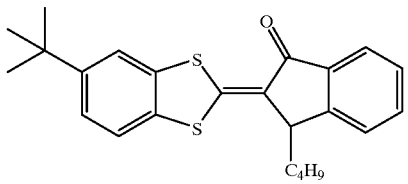
(D43) 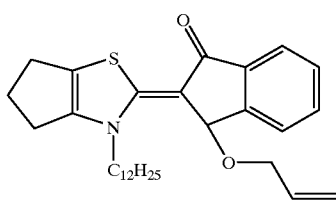

-continued (D44)
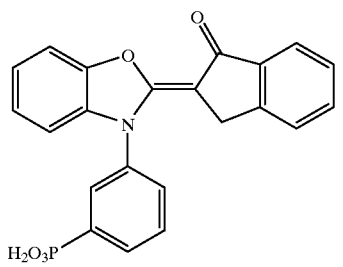

(D45)
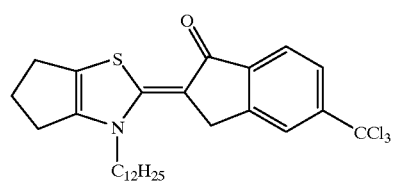

(D46)
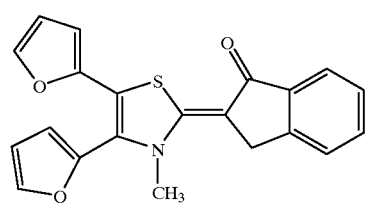

(D47)
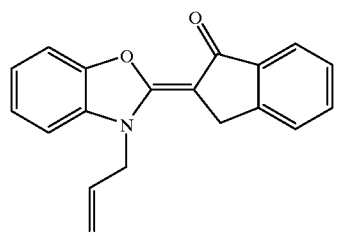

(D48)
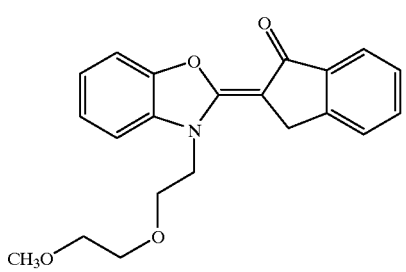

(D49)
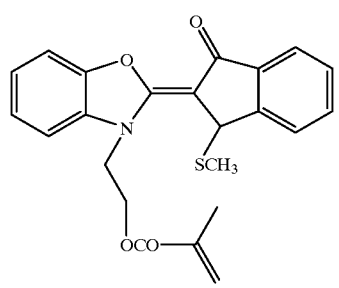

-continued (D50)
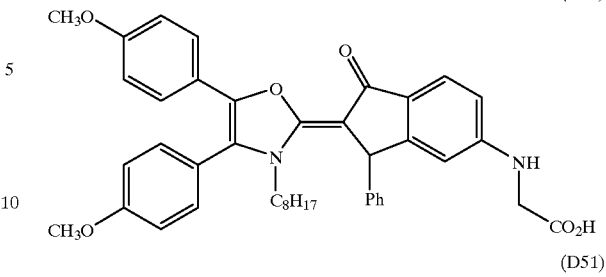

(D51)
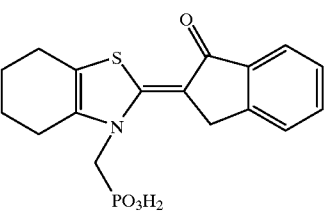

(D52)
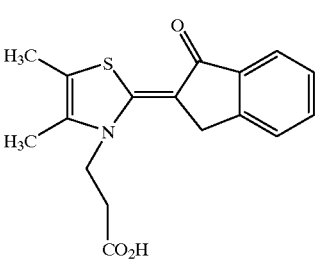

The sensitizing dye of the present invention represented by the formula (I) can be synthesized with reference, for example, to the method described by F.M. Hamer et al. in *The Cyanine Dyes and Related Compounds*, pp. 511–611 (1964) or the method described by KAI ARNE JENSEN and LARS HENRIKSEN in *ACTA CHEMICA SCANDINAVICA*, vol. 22, pp. 1107–1128 (1968).

For example, as shown in the reaction formula (1), it can be produced by the condensation reaction of a basic nucleus material having a leaving group on the carbon atom adjacent to A with an appropriate indanone derivative.

Reaction formula (I)

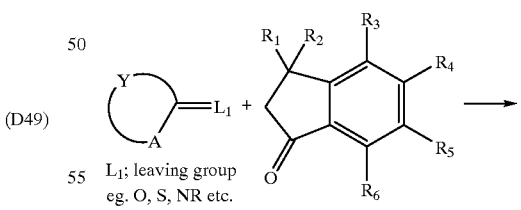

$L_1$; leaving group eg. O, S, NR etc.

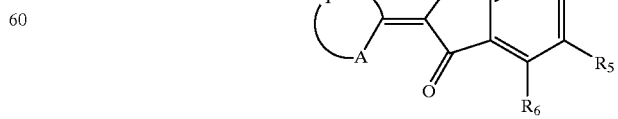

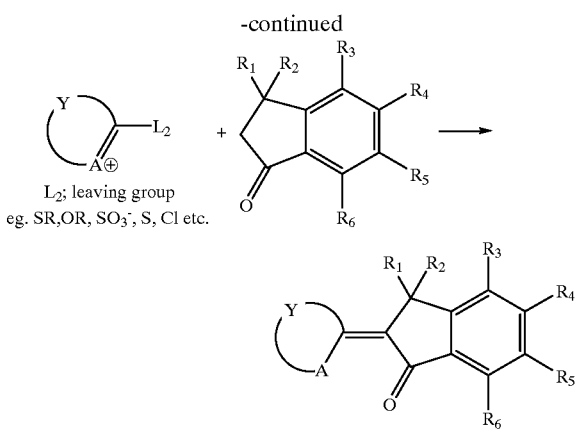

L$_2$; leaving group
eg. SR, OR, SO$_3^-$, S, Cl etc.

The method by the reaction formula (2) can be cited as a more illustrative example of preferred synthetic method. For example, a basic nucleus material having a thio group on the carbon atom adjacent to A (Ing1) is converted into a quaternary salt (Ing2) by allowing it to react with an alkylation agent (RX, such as methyl iodide or methyl tosylate) and then condensing Ing2 with an indanone derivative. As occasion demands, the condensation reaction is carried out in the presence of a base. Regarding the base, generally used bases such as amine and pyridines (e.g., trialkylamine, dimethylaminopyridine and diazabicycloundecene (DBU)), metal amides (e.g., lithium diisopropylamide), metal alkoxides (e.g., sodium methoxide and potassium t-butoxide) and metal hydrides (e.g., sodium hydride and potassium hydride) can be used without limitation. In general, since the indanone derivative is an active methylene having a relatively high pKa value, it is desirable to use a base having relatively strong basic property, while (Ing2) is decomposed in the presence of a base having high nucleophilic property. In consequence, high yield of the condensation reaction in the reaction formula (2) is obtained when a strong base with reduced nucleophilic property (e.g., sodium hydride, lithium diisopropylamide or potassium t-butoxide) is used an aprotic solvent (e.g., tetrahydrofuran (THF), diethyl ether, dioxane, dimethylformamide (DMF), benzene or toluene).

Reaction formula (2)

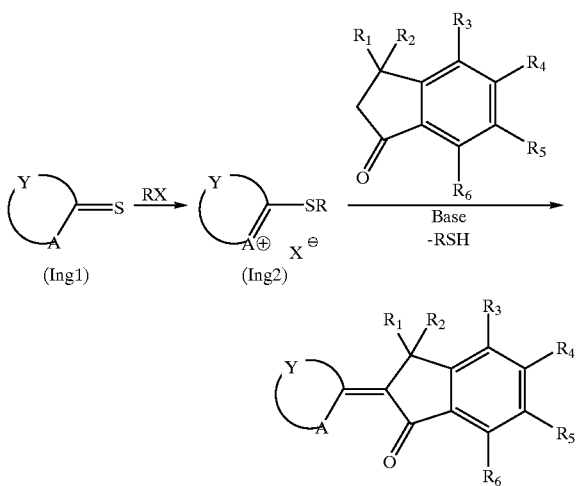

Regarding the sensitizing dye of the present invention, it is possible to carry out various chemical modifications for the purpose of improving characteristics of the photosensitive layer. For example, strength of the exposure coating can be increased and unnecessary precipitation of the dye from the coating after exposure can be inhibited, by binding the sensitizing dye to an addition-polymerizable compound structure (e.g., acryloyl group or methacryloyl group) by covalent bonding, ionic bonding, hydrogen bonding or the like means. Also, photosensitivity particularly under a low concentration condition of the initiation system can be considerably increased by binding the sensitizing dye to a titanocene compound which will be described later or to other radical generation parts (e.g., a reduction decomposing part such as alkyl halide, onium, peroxide or biimidazole, and an oxidatively cleaving a part such as borate, amine, trimethylsilylmethyl, carboxymethyl, carbonyl or imine). Also, introduction of hydrophilic parts (acidic groups or polar groups such as carboxyl group and esters thereof, sulfonic group and esters thereof and ethylene oxide group) is effective for the purpose of increasing processing aptitude for (alkali) aqueous developing solution, which is a desirable use mode of the photosensitive layer of the present invention. Particularly, ester type hydrophilic groups have such characteristics that they form a relatively hydrophobic structure in the photosensitive layer to show excellent miscibility, and also form acidic groups by their hydrolysis in the developing solution to increase hydrophilic property. In addition, in order to improve miscibility and inhibit crystallization in the photosensitive layer, substituent groups can be introduced as occasion demands. For example, in a certain photosensitive system, an unsaturated bond such as of an aryl group or allyl group is markedly effective in improving miscibility in some cases, and crystallization can be significantly inhibited when steric hindrance between dye p planes is introduced by a method such as introduction of a branched alkyl structure. Also, adhesion to an inorganic material such as a metal or a metal oxide can be improved by the introduction of phosphonic, epoxy, trialkoxysilyl or the like group. As occasion demands, polymerization of the sensitizing dye can also be applied.

Details of the use of these sensitizing dyes, such as selection of the structure, single use or joint use and amount to be added, can be optionally set corresponding to the performance design of the final photosensitive material. For example, miscibility with the photosensitive layer can be increased by jointly using two or more sensitizing dyes. In addition to the photosensitivity, molar absorption coefficient at the emission wavelength of the light source to be used is an important factor for the selection of sensitizing dye. The use of a dye having large molar absorption coefficient is economical, because it results in a relatively small amount of the dye to be added, and is also advantageous from the viewpoint of the physical properties of the photosensitive layer coating. Since photosensitivity and resolution of the photosensitive layer and physical properties of the exposure coating exert large influences upon the absorbance at the light source wavelength, amount of the sensitizing dye to be added is optionally selected by taking these factors into consideration. For example, the sensitivity is reduced at a low absorbance region of 0.1 or less. Resolution is also reduced due to influence of halation. However, for the purpose of hardening a film having a thickness of 5 mm or more, such a low absorbance is rather effective in increasing hardening degree in some cases. In addition, at a high absorption region of 3 or more, most of the light is absorbed in the photosensitive layer surface and hardening in more inner part is inhibited, so that, when used as a printing plate for example, film strength and plate adhesion become insufficient. When used as a lithographic printing plate having a relatively thin film thickness, it is desirable to set the sensitizing dye to such an amount that absorbance of the photosensitive layer becomes within the range of from 0.1 to 1.5, preferably from 0.25 to 1. When used as a lithographic printing plate, such an amount is within the range of generally from 0.05 to 30 parts by weight, preferably from 0.1 to 20 parts by weight, more preferably from 0.2 to 10 parts by weight, based on 100 parts by weight of the photosensitive layer components.

(A2) Activator Compound

The activator which is the second essential component in the photo-initiation system of the present invention is described. The activator of the present invention is a compound which generates chemical changes by its interaction with an electronic excitation condition of the sensitizing dye and thereby produces at least any one of radicals, acids and bases. Hereinafter, the radicals, acids and bases produced in this manner are simply referred to as active species. When these compounds are not present or the activator alone is used, practically sufficient sensitivity cannot be obtained, but, as an embodiment in which the aforementioned sensitizing dye and an active compound are jointly used, it is possible to use them as a single compound by employing an appropriate chemical method (e.g., linkage of the sensitizing dye and activator compound through a chemical bond).

Such a technical concept is disclosed for example in JP-A-2-63054.

In general, it is considered that most of these activators produce active species through the following initial chemical processes (1) to (3). That is, (1) reductive decomposition of the activator, based on the electron transfer reaction from the electronic excitation condition of the sensitizing dye to the activator, (2) oxidative decomposition of the activator, based on the electron transfer from the activator to the electronic excitation condition of the sensitizing dye and (3) decomposition of the activator from its electronic excitation condition, based on the energy transfer from the electronic excitation condition of the sensitizing dye to the activator. Though there are many ambiguous cases regarding which activator compound belongs to which of the types (1) to (3), a remarkable characteristic nature of the sensitizing dye of the present invention is that its combination with any of these activator types exerts markedly high sensitization effect.

The activator compounds known to those skilled in the art can be used without limitation, and many of their illustrative examples are described for example by Bruce M. Monroe et al. in *Chemical Review*, 93, 435 (1993), by R. S. Davidson in *Journal of Photochemistry and Biology A: Chemistry*, 73, 81 (1993), by J. P. Faussier in "Photoinitiated Polymerization—Theory and Applications": Rapra Review, vol. 9, Report, Rapra Technology (1998) and by M. Tsunooka et al. in *Prog. Polym. Sci.*, 21, 1 (1996). Also, regarding other compounds having functions of the aforementioned types (1) and (2), a group of compounds which undergo oxidative or reductive bond cleavage are also known, such as those which are described by F. D. Saeva in *Topics in Current Chemistry*, 156, 59 (1990), G. G. Maslak in *Topics in Current Chemistry*, 168, 1 (1993), H. B. Shuster et al in *JACS*, 112, 6329 (1990) and I. D. F. Eaton et al in *JACS*, 102, 3298 (1980).

Illustrative examples of desirable activators are described in the following by classifying them into (a) activators which produce active species by undergoing reductive bond cleavage, (b) activators which produce active species by undergoing oxidative bond cleavage and (c) other activators, though the present invention is not restricted by the description on these reaction mechanisms, because there are many cases having no popular views regarding which compound belongs to which of these types.

(a) Activators which produce active species by undergoing reductive bond cleavage.

Compound having carbon-halogen bond: considered to generate active species by reductive cleavage of carbon-halogen bond (described for example in *Polymer Preprints, Jpn*, 41 (3), 542 (1992)). As the active species, radicals and acids can be generated. As illustrative examples, halomethyl-s-triazines, halomethyloxadiazoles which can be synthesized easily by those skilled in the art by the synthetic method described by M. P. Hutt, E. F. Elslager and L. M. Merbel in *Journal of Heterocyclic chemistry*, 7, 511 (1970) and the compounds described in German Patents 2641100, 3333450, 3021590 and 3021599 can be suitably used.

Compound having nitrogen-nitrogen bond or nitrogenous heterocycle-nitrogenous heterocycle bond: generates reductive bond cleavage (described for example in *J. Pys. Chem.*, 96, 207 (1992)). As illustrative examples, hexaarylbiimidazoles are suitably used. The active species formed is lophine radical which initiates radical chain reaction by the joint use of a hydrogen donor as occasion demands, and image formation using oxidation reaction by lophine radical is also known (describedfor example in *J. Imaging Sci.*, 30, 215 (1986)).

Compound having oxygen-oxygen bond: considered to generate active radicals by reductive cleavage of oxygen-oxygen bond (described for example in *Polym. Adv. Technol.*, 1, 287 (1990). As illustrative examples, organic peroxides are suitably used. Radicals can be generated as the active species.

Onium compound: considered to generate active species by reductive cleavage of carbon-hetero bond or oxygen-nitrogen bond (described for example in *J. Photopolym. Sci. Technol.*, 3, 149 (1990)). Its useful illustrative examples include iodonium salts described in European Patent 104143, U.S. Pat. No. 4, 837, 124, JP-A-2-150848 and JP-A-2-96514, sulfonium salts described in European Patent 370693, European Patent 233567, European Patent 297443, European Patent 297442, European Patent 279210, European Patent 422570, U.S. Pat. No. 3,902,144, U.S. Pat. No. 4,933,377, U.S. Pat. No. 4,760,013, U.S. Pat. No. 4,734,444 and U.S. Pat. No. 2,833,827, diazonium salts (e.g., benzene-diazonium which may have a substituent group), diazonium salt resins (e.g., formaldehyde resin of diazodiphenylamine), N-alkoxypyridinium salts (e.g., those which are described in U.S. Pat. No. 4,743,528, JP-A-63-138345, JP-A-63-142345, JP-A-63-142346 and JP-B-46-42363 (the term "JP-B" as used herein means an "examined Japanese patent publication"), such as 1-methoxy-4-phenylpyridinium tetrafluoroborate) and the compounds described in JP-B-52-147277, JP-B-52-14278 and JP-B-52-14279. Radicals and acids are generated as the active species.

Active esters: esters such as nitrobenzyl esters of sulfonic acid and carboxylic acid, esters of sulfonic acid and carboxylic acid with N-hydroxy compounds (e.g., N-hydroxyphthalimide and oxime), sulfonic acid esters of pyrogallol and naphthoquinonediazido-4-sulfonic acid esters can be decomposed reductively. As the active species, radicals and acids can be generated. Illustrative examples of the sulfonic acid esters include nitrobenzyl ester compounds described in European Patent 0290750, European Patent 046083, European Patent 156153, European Patent 271851, European Patent 0388343, U.S. Pat. No. 3,901,710, U.S. Pat. No. 4,181,531, JP-A-60-198538 and JP-A-53-133022, iminosulfonate compounds described in European Patent 0199672, European Patent 84515, European Patent 199672, European Patent 044115, European Patent 0101122, U.S. Pat. No. 4,618,564, U.S. Pat. No. 4,371,605, U.S. Pat. No. 4,431,774, JP-A-64-18143, JP-A-2-245756 and JP-A-4-365048 and the compounds described in JP-B-62-6223, JP-B-63-14340 and JP-A-59-174831, as well the compounds shown below.

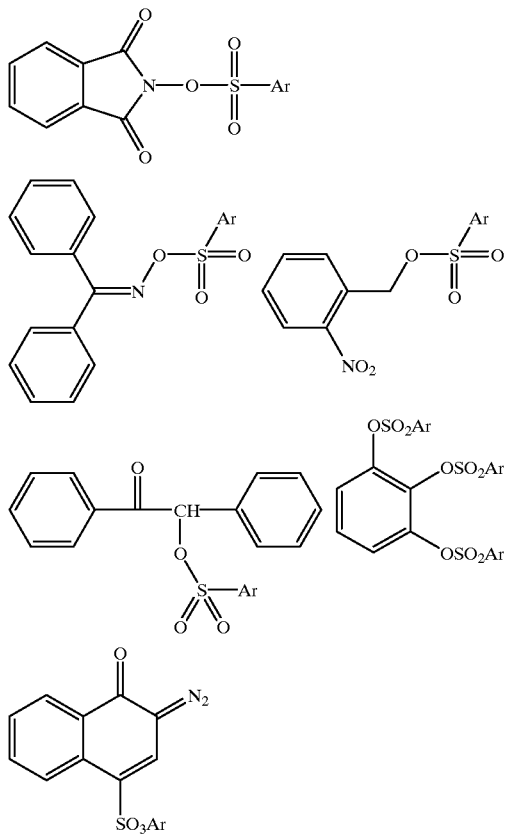

(In the above formulae, Ar represents an aromatic or aliphatic group which may be substituted.)

In addition, it is possible to produce bases as the active species, and the following compounds are known for example.

Ferrocene and iron allene complexes: active radicals can be produced reductively. Illustratively, they are disclosed for example in JP-A-1-304453 and JP-A-1-152109.

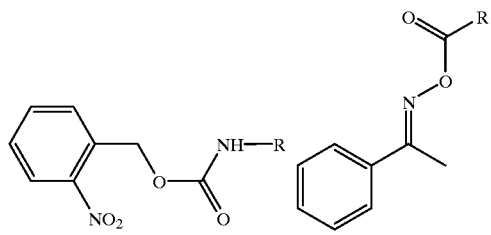

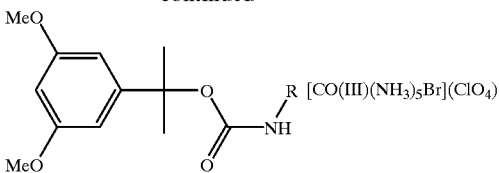

(In the above formulae, R represents an aromaric or aliphatic group which may be substituted.)

Disulfones: acids can be generated by causing reductive cleavage of S—S bond. For example, diphenyldisulfones described in JP-A-61-166544 are known.

(b) Activators which produce active species by undergoing oxidative bond cleavage.

Alkylate complex: considered to form active radicals by oxidative cleavage of carbon-hetero bond (e.g., described in J. Am. Chem. Soc., 112, 6329 (1990)). Illustratively, triaryl alkylborates are suitably used.

Alkylamine compound: considered to form active radicals by oxidative cleavage of C—X bond on the carbon adjacent to nitrogen (e.g., described in J. Am. Chem. Soc., 116, 4211 (1994)). Preferred examples of X include hydrogen atom, carboxyl group, trimethylsilyl group and benzyl group. Illustratively, ethanolamines, N-phenylglycines and N-trimethylsilylmethylanilines can be exemplified.

Sulfur- or tin-containing compound: a compound in which nitrogen atom of the aforementioned amines is replaced by sulfur or tin atom can form active radicals by the same action. Also, it is known that a compound having S—S bond can effect sensitization by S—S cleavage.

α-Substituted methylcarbonyl compound: active radicals can be formed by oxidative cleavage of carbonyl-α carbon bond. Similar compound in which carbonyl is converted into oxime ether also shows the same action. Illustrative examples include 2-alkyl-1-[4-(alkylthio)phenyl]-2-morpholinopulonone-1 compounds and oxime ethers obtained by allowing these compounds to react with hydroxyamines and then carrying out etherification of N—OH.

Sulfinic acid salts: active radicals can be formed reductively. Illustratively, sodium arylsulfinate can be exemplified.

(c) Other activators

Though the sensitization mechanism is not clear, there are many compounds capable of functioning as activators. Their examples include organic metal compounds such as titanocene and ferrocene, aromatic ketones, acylphosphines and biacylphosphines, and they can generate radicals and acids as the active species.

Among the activator compounds to be used in the present invention, preferred compounds having excellent sensitivity and stability are illustratively described in the following.

(1) Halomethyltriazines

Compounds represented by the following formula [II] can be exemplified. They are particularly excellent in terms of radical generation and acid generation abilities.

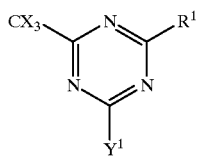

[II]

In the formula [II], X represents a halogen atom, $Y^1$ represents —$CX_3$, —$NH_2$, —$NHR^{1'}$, $NR^{1'}_2$ or —$OR^{1'}$, wherein $R^{1'}$ represents an alkyl group, a substituted alkyl group, an aryl group or a substituted aryl group, and $R^1$ represents —$CX_3$, an alkyl group, a substituted alkyl group, an aryl group, a substituted aryl group or a substituted alkenyl group.

Illustrative examples of such compounds include the compounds described by Wakabayashi et al. in *Bull. Chem. Soc. Japan*, 42, 2924 (1969), such as 2-phenyl-4,6-bis (trichloromethyl)-S-triazine, 2-(p-chlorophenyl)-4,6-bis (trichloromethyl)-S-triazine, 2-(p-tolyl)-4,6-bis (trichloromethyl)-S-triazine, 2-(p-methoxyphenyl)-4,6-bis (trichloromethyl)-S-triazine, 2-(2',4'-dichlorophenyl)-4,6-bis(trichloromethyl)-S-triazine, 2,4,6-tris(trichloromethyl)-S-triazine, 2-methyl-4,6-bis(trichloromethyl)-S-triazine, 2-n-nonyl-4,6-bis(trichloromethyl)-S-triazine and 2-(α,α,β-trichloroethyl)-4,6-bis(trichloromethyl)-S-triazine. Other examples include the compounds described in the specification of British Patent 1388492, such as 2-(styryl-4,6-bis (trichloromethyl)-S-triazine, 2-(p-methylstyryl)-4,6-bis (trichloromethyl)-S-triazine, 2-(p-methoxystyryl)-4,6-bis (trichloromethyl)-S-triazine and 2-(p-methoxystyryl)-4-amino-6-trichloromethyl-S-triazine, the compounds described in JP-A-53-133428, such as 2-(4-methoxy-naphtho-1-yl)-4,6-bis-trichloromethyl-S-triazine, 2-(4-ethoxy-naphtho-1-yl)-4,6-bis-trichloromethyl-S-triazine, 2-[4-(2-ethoxyethyl)-naphtho-1-yl]-4,6-bis-trichloromethyl-S-triazine, 2-(4,7-dimethoxy-naphtho-1-yl)-4,6-bis-trichloromethyl-S-triazine and 2-(acenaphtho-5-yl)-4,6-bis-trichloromethyl-S-triazine, and the compounds described in the specification of German Patent 3337024, such as the following compounds.

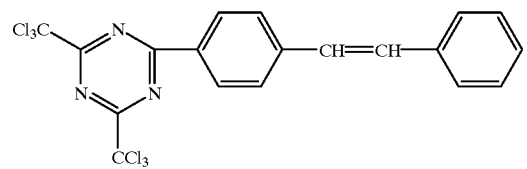

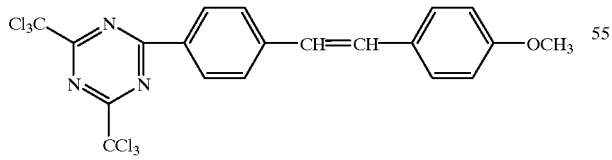

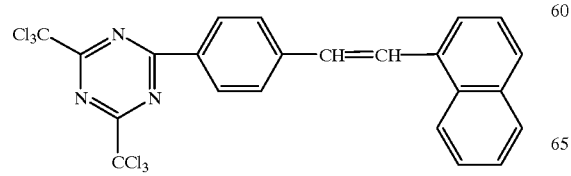

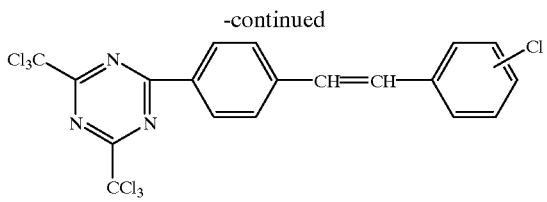

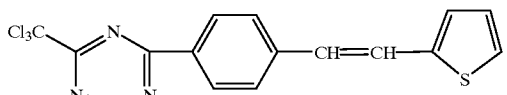

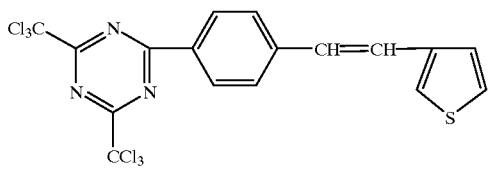

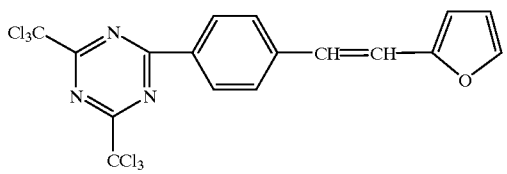

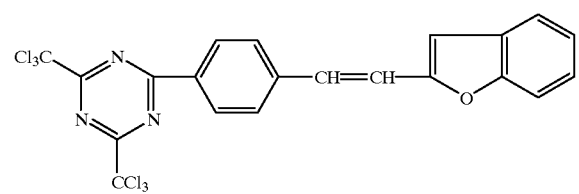

Also can be exemplified are the compounds described by F. C. Schaefer et al. in *J. Org. Chem.*, 29, 1527 (1964), such as 2-methyl-4,6-bis(tribromomethyl)-S-triazine, 2,4,6-tris (tribromomethyl)-S-triazine, 2,4,6-tris(tribromomethyl)-S-triazine, 2,4,6-tris(dibromomethyl)-S-triazine, 2-amino-4-methyl-6-tribromomethyl-S-triazine and 2-methoxy-4-methyl-6-trichloromethyl-S-triazine.

Also can be exemplified are the compounds described in JP-A-62-58241, such as the following compounds.

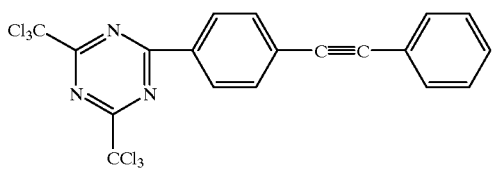

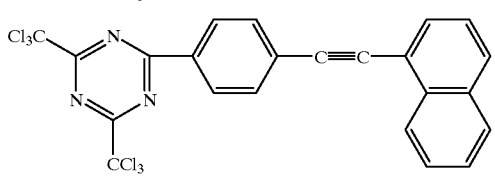

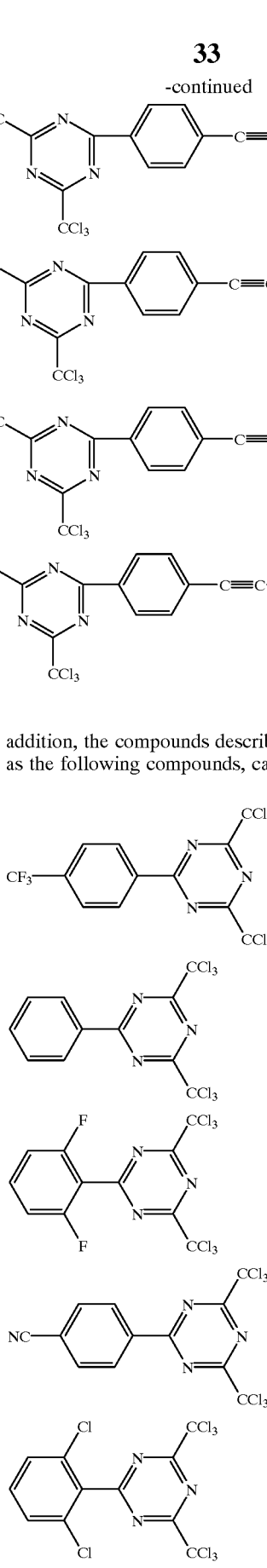

In addition, the compounds described in JP-A-5-281728, such as the following compounds, can also be exemplified.

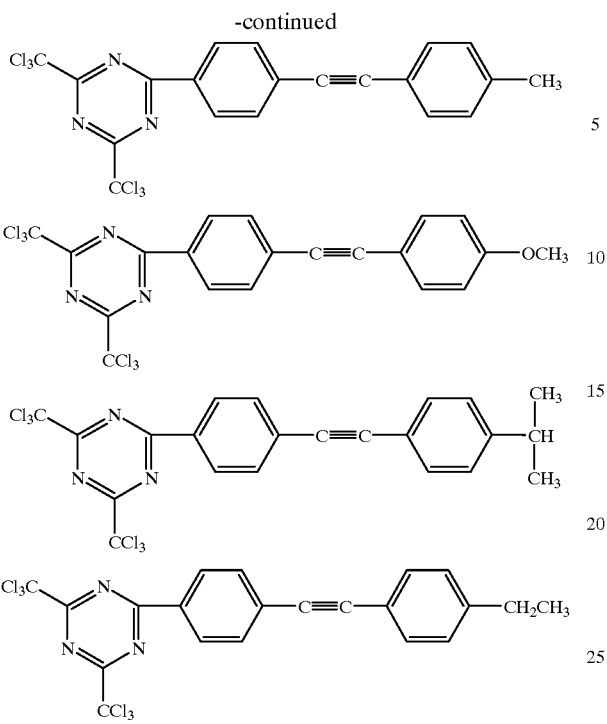

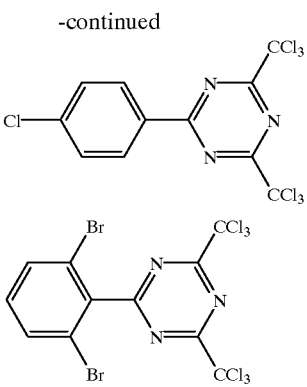

(2) Titanocenes

The titanocene compound to be used particularly desirably as the activator is any titanocene compound which can generate active species when irradiated with light in the coexistence of the aforementioned sensitizing dye, and it can be used by optionally selecting from known compounds described, for example, in JP-A-59-152396, JP-A-61-151197, JP-A-63-41483, JP-A-63-41484, JP-A-2-249, JP-A-2-291, JP-A-3-27393, JP-A-3-12403 and JP-A-6-41170.

Its illustrative examples include di-cyclopentadienyl-Ti-di-chloride, di-cyclopentadienyl-Ti-bis-phenyl, di-cyclopentadienyl-Ti-bis-2,3,4,5,6-pentafluorophen-1-yl, di-cyclopentadienyl-Ti-bis-2,3,5,6-tetrafluorophen-1-yl, di-cyclopentadienyl-Ti-bis-2,4,6-trifluorophen-1-yl, di-cyclopentadienyl-Ti-bis-2,6-difluorophen-1-yl, di-cyclopentadienyl-Ti-bis-2,4-difluorophen-1-yl, di-methylcyclopentadienyl-Ti-bis-2,3,4,5,6-pentafluorophen-1-yl, di-methylcyclopentadienyl-Ti-bis-2,3,5,6-tetrafluorophen-1-yl, di-methylcyclopentadienyl-Ti-bis-2,4-difluorophen-1-yl and bis(cyclopentadienyl)-bis(2,6-difluoro-3-(pir-1-yl)phenyl)titanium.

(3) Borate Salt Compounds

Borate salts represented by the following formula [III] show excellent radical generation ability.

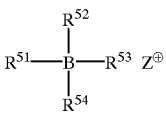

[III]

In the formula [III], $R^{51}$, $R^{52}$, $R^{53}$ and $R^{54}$ may be the same or different from one another and each represents a substituted or unsubstituted alkyl group, a substituted or unsubstituted aryl group, a substituted or unsubstituted alkenyl group, a substituted or unsubstituted alkynyl group or a substituted or unsubstituted heterocyclic group, wherein two or more groups of $R^{51}$, $R^{52}$, $R^{53}$ and $R^{54}$ may together form a cyclic structure, with the proviso that at least one of $R^{51}$, $R^{52}$, $R^{53}$ and $R^{54}$ is a substituted or unsubstituted alkyl group, and $Z^+$ represents an alkali metal cation or a quaternary ainramonium cation.

The alkyl group of $R^{51}$ to $R^{54}$ include straight, branched and cyclic groups, preferably having from 1 to 18 carbon atoms. Its illustrative examples include methyl, ethyl, propyl, isopropyl, butyl, pentyl, hexyl, octyl, stearyl, cyclobutyl, cyclopentyl and cyclohexyl. Also, examples of the substituted alkyl group include the above-described alkyl group further having a substituent group such as a halogen atom (e.g., —Cl or —Br), cyano group, nitro group, an aryl group (preferably phenyl group), hydroxy group, a group of the following formula

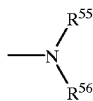

(wherein each of $R^{55}$ and $R^{56}$ independently represents hydrogen atom, an alkyl group having from 1 to 14 carbon atoms or an aryl group), —COOR$^{57}$ (wherein $R^{57}$ represents hydrogen atom, an alkyl group having from 1 to 14 carbon atoms or an aryl group), —COOR$^{58}$ or —OR$_{58}$ (wherein $R^{58}$ represents an alkyl group having from 1 to 14 carbon atoms or an aryl group and $R^{59}$ represents hydrogen atom, an alkyl group having from 1 to 14 carbon atoms or an aryl group).

Examples of the aforementioned aryl group of $R^{51}$ to $R^{54}$ include aryl groups having from 1 to 3 rings, such as phenyl group and naphthyl group, and examples of the substituted aryl group include the above-described aryl groups further having a substituent group of the aforementioned substituted alkyl group or having an alkyl group of from 1 to 14 alkyl group.

Examples of the aforementioned alkenyl group of $R^{51}$ to $R^{54}$ include straight, branched and cyclic groups having from 2 to 18 carbon atoms, and examples of the substituent group of substituted alkenyl group include the aforementioned substituent groups of substituted alkyl group.

Examples of the aforementioned alkynyl group of $R^{51}$ to $R^{54}$ include straight or branched groups having from 2 to 28 carbon atoms, and examples of the substituent group of substituted alkynyl group include the aforementioned substituent groups of substituted alkyl group.

Also, examples of the aforementioned heterocyclic group of $R_{52}$ to $R^{54}$ include heterocyclic groups of five-membered rings or more, preferably from five- to seven-membered rings, containing at least one of N, S and O, and a condensed ring may be included in the heterocyclic ring. It may also have a substituent group selected from the aforementioned substituent groups of substituted aryl group.

Illustrative examples of the compound represented by the formula [III] include those which are described in U.S. Pat. No. 3,567,453, U.S. Pat. No. 4,343,891, European Patent 109772 and European Patent 109773 and the compounds shown in the following.

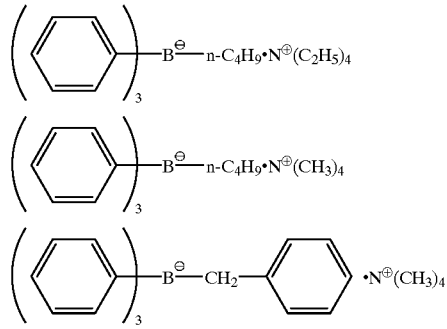

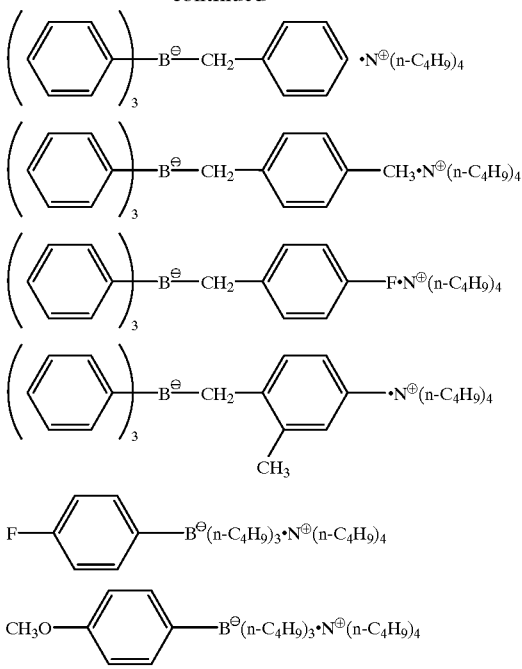

(4) Hexaarylbiimidazoles

These compounds have excellent stability and can perform high sensitivity radical generation. Their illustrative examples include 2,2'-bis(o-chlorophenyl)-4,4',5,5'-tetraphenylbiimidazole, 2,2'-bis(o-bromophenyl)-4,4',5,5'-tetraphenylbiimidazole, 2,2'-bis(o,p-dichlorophenyl)-4,4',5,5'-tetraphenylbiimidazole, 2,2'-bis(o-chlorophenyl)-4,4',5,5'-tetra(m-methoxyphenyl)biimidazole, 2,2'-bis(o,o'-dichlorophenyl)-4,4',5,5'-tetraphenylbiimidazole, 2,2'-bis(o-nitrophenyl)-4,4',5,5'-tetraphenylbiimidazole, 2,2'-bis(o-methylphenyl)-4,4',5,5,-tetraphenylbiimidazole and 2,2'-bis(o-trifluoromethylphenyl)-4,4',5,5'-tetraphenylbiimidazole.

(5) Onium Salt Compounds

Onium compounds of the elements of the 15 (5B), 16 (6B) and 17 (7B) groups in the periodic table, illustratively N, P, As, Sb, Bi, O, S, Se, Te and I, are activators having superior sensitivity. Particularly, iodonium salts and sulfonium salts, most particularly diaryliodonium and triarylsulfonium salt compounds, are markedly excellent in terms of both sensitivity and storage stability. These compounds can generate acids and/or radicals which can be properly used by optionally selecting the application conditions depending on each purpose. The following compounds are cited as illustrative examples.

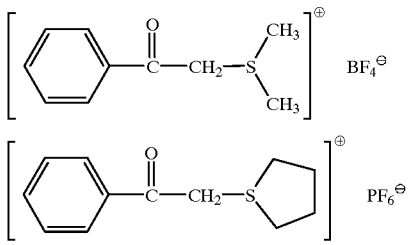

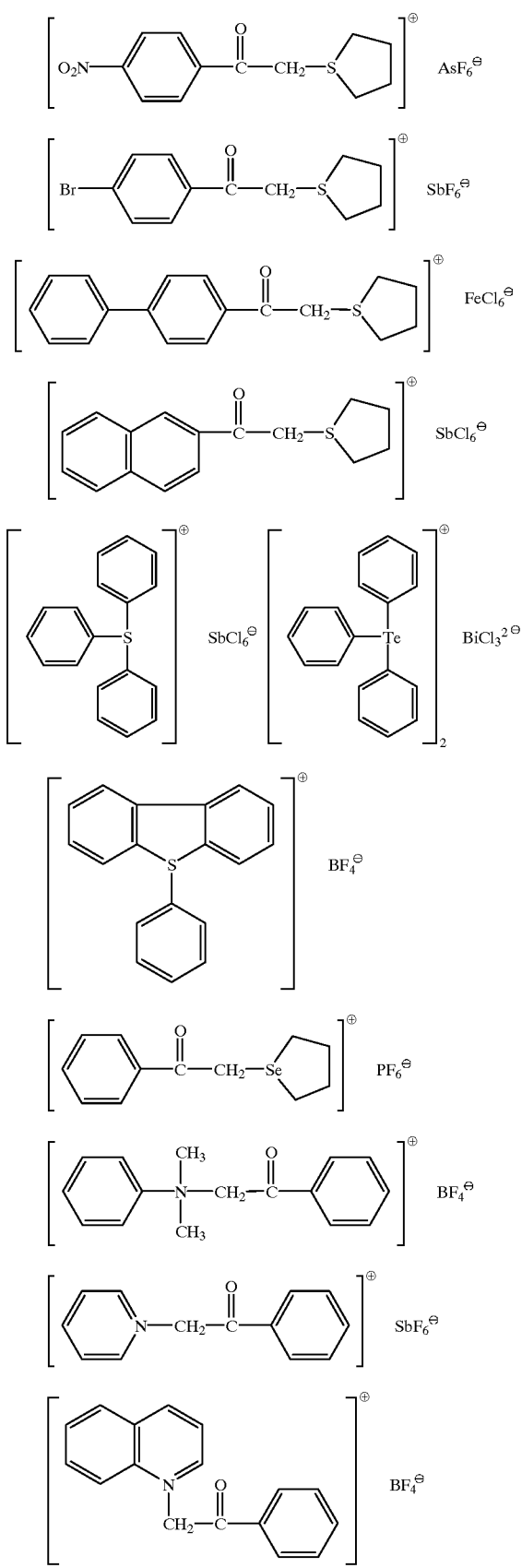
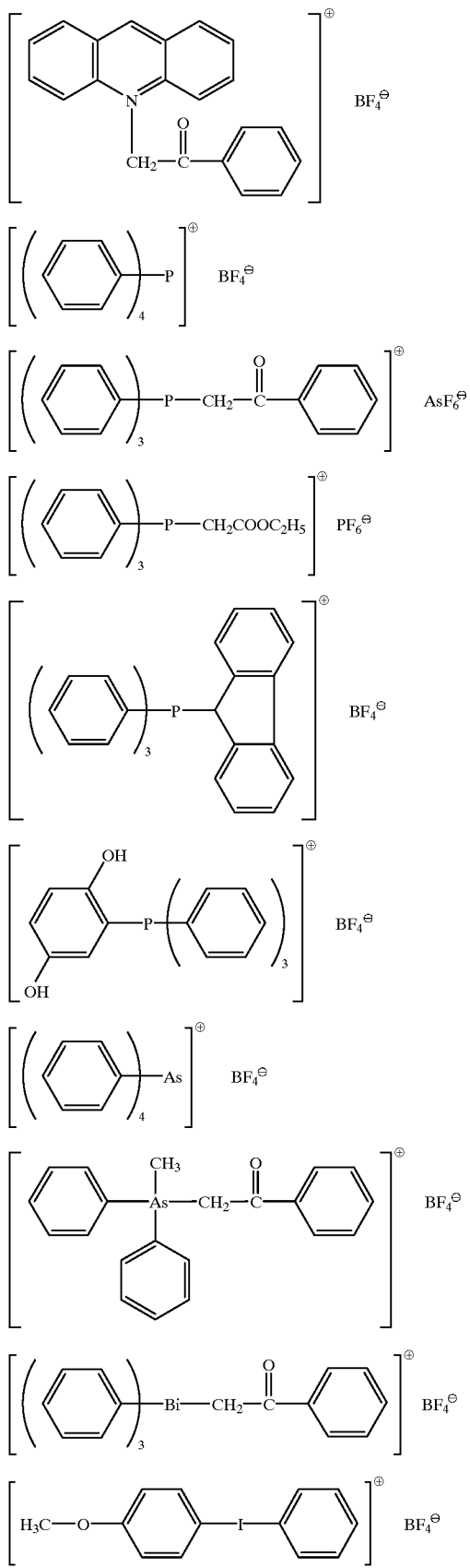

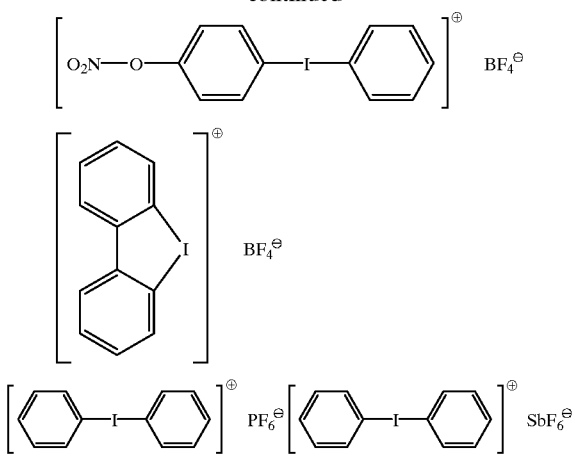

(6) Organic Peroxide

When an organic peroxide type activator is used, generation of radicals as active species can be effected with markedly high sensitivity.

Regarding the (c) "organic peroxide" as another example of the component (ii) to be used in the present invention, almost all of organic compounds having at least one oxygen-oxygen bond in one molecule are included therein, and its examples include methyl ethyl ketone peroxide, cyclohexanone peroxide, 3,3,5-trimethylcyclohexanone peroxide, methylcyclohexanone peroxide, acetylacetone peroxide, 1,1-bis(t-butylperoxy)-3,3,5-trimethylcyclohexane, 1,1-bis (t-butylperoxy)cyclohexane, 2,2-bis(t-butylperoxy)butane, t-butyl hydroperoxide, cumene hydroperoxide, diisopropylbenzene hydroperoxide, paramethane hydroperoxide, 2,5-dimethylhexane-2,5-dihydroperoxide, 1,1,3,3-tetramethylbutyl hydroperoxide, di-t-butyl peroxide, t-butylcumyl peroxide, dicumyl peroxide, bis(t-butylperoxyisopropyl)benzene, 2,5-dimethyl-2,5-di(t-butylperoxy)hexane, 2,5-dimethyl-2,5-di(t-butylperoxy) hexyne-3, acetyl peroxide, isobutyryl peroxide, octanoyl peroxide, decanoyl peroxide, lauroyl peroxide, 3,5,5-trimethylhexanoyl peroxide, succinic acid peroxide, benzoyl peroxide, 2,4-dichlorobenzoyl peroxide, meta-toluoyl peroxide, diisopropyl peroxydicarbonate, di-2-ethylhexyl peroxydicarbonate, di-2-ethoxyethyl peroxydicarbonate, dimethoxyisopropyl peroxycarbonate, di(3-methyl-3-methoxybutyl) peroxydicarbonate, t-butyl peroxyacetate, t-butyl peroxypivalate, t-butyl peroxyneodecanoate, t-butyl peroxyoctanoate, t-butyl peroxy-3,5,5-trimethylhexanoate, t-butyl peroxylaurate, t-butyl peroxybenzoate, di-t-butyl peroxyisophthalate, 2,5-dimethyl-2,5-di(benzoylperoxy) hexane, t-butyl permaleate, t-butyl peroxyisopropylcarbonate, 3,3',4,4'-tetra-(t-butylperoxycarbonyl)benzophenone, 3,3',4,4'-tetra-(t-amylperoxycarbonyl)benzophenone, 3,3',4,4'-tetra-(t-hexylperoxycarbonyl)benzophenone, 3,3',4,4'-tetra-(t-octylperoxycarbonyl)benzophenone, 3,3',4,4'-tetra-(cumylperoxycarbonyl)benzophenone, 3,3',4,4'-tetra-(p-isopropylcumylperoxycarbonyl)benzophenone, carbonyl di(t-butylperoxydihydrogendiphthalate) and carbonyl di(t-hexylperoxydihydrogendiphthalate).

Preferred among these compounds are peroxide ester systems such as 3,3',4,4'-tetra-(t-butylperoxycarbonyl) benzophenone, 3,3',4,4'-tetra-(t-amylperoxycarbonyl) benzophenone, 3,3',4,4'-tetra-(t-hexylperoxycarbonyl) benzophenone, 3,3',4,4'-tetra-(t-cumylperoxycarbonyl) benzophenone, 3,3',4,4'-tetra-(cumylperoxycarbonyl) benzophenone, 3,3',4,4'-tetra-(p-isopropylcumylperoxycarbonyl)benzophenone and di-t-butyl diperoxyisophthalate.

Regarding these activators described above, it is possible to carry out various chemical modifications for the purpose of improving characteristics of the photosensitive layer, similar to the case of the aforementioned sensitizing dyes. For example, various methods can be employed, such as their binding to the sensitizing dyes, addition-polymerizable unsaturated compounds and other activator parts, introduction of hydrophilic parts, improvement of miscibility and introduction of substituent groups for inhibiting crystallization or for improving adhesion, as well as their polymerization.

Also, similar to the case of the aforementioned sensitizing dyes, application method of these activator compounds can be optionally set based on the performance designing of the photosensitive material. For example, miscibility with the photosensitive layer can be increased by joint use of two or more of these compounds. Larger amount of the activator compound to be used is generally advantageous in terms of the photosensitivity, and sufficient photosensitivity can be obtained when the compound is used in an amount of from 0.5 to 80 parts by weight, preferably from 1 to 50 parts by weight, based on 100 parts by weight of the photosensitive layer components. On the other hand, when the activator itself has absorption in visible light like the case of titanocene compounds, it is desirable to use smaller amounts of the activator in view of yellow or the like fog caused by a light of around 500 nm, in using under a white light, but sufficient photosensitivity can be obtained even if the amount of activator compound to be used is reduced to 6 parts by weight or less, fuirther to 1.9 parts by weight or less, more further to 1.4 parts by weight or less, by its combination with the sensitizing dye of the present invention.

[B] Component (iii)

The third essential component (iii) of the present invention is a compound whose physical or chemical characteristics are changed and maintained by the action of the active species formed by light reaction of the aforementioned photo-initiation system, and any optional compound having such properties can be used as the component (iii) with no particular limitation; for example, a number of the compounds exemplified in relation to the aforementioned initiation system have such properties. Characteristics of the component (iii) changed by the radicals, acids and/or bases formed from the photo-initiation system include changes in the molecular physical properties such as absorption spectrum (color), chemical structure and polarizability and the material-based physical properties such as solubility, strength, index of refraction, fluidity and adhesive property.

For example, when a compound whose absorption spectrum is changed by pH, such as a pH indicator, is used as the component (iii), and an acid or base is generated from the initiation system, color tone of the exposure region can be changed selectively, and such a composition is useful as an image forming material. In the same manner, when a compound whose absorption spectrum is changed by oxidation, reduction or nucleophilic addition reaction is used as the component (iii), image formation can be effected by inducing oxidation, reduction or the like reaction by radicals formed from the initiation system. Such a case is disclosed for example in *J. Am. Chem. Soc.*, 108, 128 (1986), *J. Imaging. Sci.*, 30, 215 (1986) and *Israel. J. Chem.*, 25, 264 (1986).

Also, a photo-curing resin or negative type photopolymer can be formed by using an addition-polymerizable or polycondensation-polymerizable compound as the component (iii) in combination with the initiation system.

As the component (iii), radical polymerization compounds (e.g., a compound having ethylenic unsaturated bond), cationic polymerization compounds (e.g., an epoxy compound, a vinyl ether compound and a methylol compound) and anionic polymerization compounds (e.g., an epoxy compound) are used, and such cases are described for example in Photopolymer Handbook, edited by Photopolymer Meeting, published by Industrial Examination Association (translation from Japanese), and *High Polymer* (Japanese), 45, 786 (1996). A composition in which a thiol compound is used as the component (iii) in combination with an optical radical generation system is also well known.

It is also effective to use an acid-decomposable compound as the component (iii) in combination with a photo acid generator. For example, a material prepared from a polymer having acid-decomposable side and principal chains, in which its solubility or hydrophilic or hydrophobic property is changed by light, is broadly used in practice as an optically decomposing photosensitive resin or a positive type photopolymer. Illustrative examples of such a material is described for example in ACS. Symp. Ser. 242, 11 (1984), JP-A-60-3625, U.S. Pat. No. 5,102,771, U.S. Pat. No. 5,206,317, U.S. Pat. No. 5,212,047, JP-A-26850, JP-A-3-1921731, JP-A-60-10247 and JP-A-62-40450.

The following more illustratively describes the addition-polymerizable compound as a component (iii) which is particularly useful for the purpose of obtaining high sensitivity lithographic printing plates, as one of the objects of the present invention. (B-1) Addition-polymerizable compound The addition-polymerizable compound having at least one ethylenic unsaturated double bond, as a desirable component (iii) to be used in the present invention, is selected from compounds having at least one, preferably two or more, of the terminal ethylenic unsaturated double bond. Such compounds are widely known in said industrial field and can be used in the present invention with no particular limitation. These compounds have certain chemical forms such as monomers, prepolymers, namely dimers, trimers and oligomers, or mixtures thereof and copolymers thereof. Unsaturated carboxylic acids (e.g., acrylic acid, methacrylic acid, itaconic acid, crotonic acid, isocrotonic acid and maleic acid) and esters or amides thereof can be exemplified as the monomers and copolymers thereof, and esters of unsaturated carboxylic acids with aliphatic polyhydric alcohol compounds and amides of unsaturated carboxylic acids with aliphatic polyhydric amine compounds are preferably used. Also to be used preferably are addition products of monofunctional or multifunctional isocyanates or epoxy compounds, or dehydration condensation products of monofunctional or multifunctional carboxylic acids, with unsaturated carboxylic acid esters or amides having nucleophilic substituent groups (e.g., hydroxyl group, amino group, mercapto group and the like). Also preferred are addition products of unsaturated carboxylic acid esters or amides having electrophilic substituent groups (e.g., isocyanato group, epoxy group and the like) with monofunctional or multifunctional alcohols, amines or thiols, and substitution products of unsaturated carboxylic acid esters or amides having leaving substituent groups (e.g., halogen group, tosyloxy group and the like) with monofunctional or multifunctional alcohols, amines or thiols. As other examples, derivatives of these compounds in which the unsaturated carboxylic acid is replaced by unsaturated phosphonic acid, styrene or vinyl ether can also be used.

Regarding the monomer of esters of aliphatic polyhydric alcohol compounds with unsaturated carboxylic acids, illustrative examples of acrylic acid esters include ethylene glycol diacrylate, triethylene glycol diacrylate, 1,3-butanediol diacrylate, tetramethylene glycol diacrylate, propylene glycol diacrylate, neopentyl glycol diacrylate, trimethylolpropane triacrylate, trimethylolpropane tri(acryloyloxypropyl) ether, trimethylolethane triacrylate, hexanediol diacrylate, 1,4-cyclohexanediol diacrylate, tetraethylene glycol diacrylate, pentaerythritol diacrylate, pentaerythritol triacrylate, pentaerythritol tetraacrylate, dipentaerythritol diacrylate, dipentaerythritol hexaacrylate, sorbitol triacrylate, sorbitol tetraacrylate, sorbitol pentaacrylate, sorbitol hexaacrylate, tri(acryloyloxyethyl) isocyanurate and polyester acrylate oligomer.

Examples of methacrylic acid esters include tetramethylene glycol dimethacrylate, triethylene glycol dimethacrylate, neopentyl glycol dimethacrylate, trimethylolpropane trimethacrylate, trimethylolethane trimethacrylate, ethylene glycol dimethacrylate, 1,3-butanediol dimethacrylate, hexanediol dimethacrylate, pentaerythritol dimethacrylate, pentaerythritol trimethacrylate, pentaerythritol tetramethacrylate, dipentaerythritol dimethacrylate, dipentaerythritol hexamethacrylate, sorbitol trimethacrylate, sorbitol tetramethacrylate, bis[p-(3-methacryloxy-2-hydroxypropoxy)phenyl]dimethylmethane and bis[p-(methacryloxyethoxy)phenyl]dimethylmethane.

Examples of itaconic acid esters include ethylene glycol diitaconate, propylene glycol diitaconate, 1,3-butanediol diitaconate, 1,4-butanediol diitaconate, tetramethylene glycol diitaconate, pentaerythritol diitaconate and sorbitol tetraitaconate.

Examples of crotonic acid esters include ethylene glycol dicrotonate, tetramethylene glycol dicrotonate, pentaerythritol dicrotonate and sorbitol tetradicrotonate.

Examples of isocrotonic acid esters include ethylene glycol diisocrotonate, pentaerythritol diisocrotonate and sorbitol tetraisocrotonate.

Examples of maleic acid esters include ethylene glycol dimaleate, triethylene glycol dimaleate, pentaerythritol dimaleate and sorbitol tetramaleate.

As other examples of esters, the aliphatic alcohol esters described in JP-B-46-27926, JP-B-51-47334 and JP-A-57-196231, the esters having aromatic nuclei described in JP-A-59-5240, JP-A-59-5241 and JP-A-2-226149 and the esters containing amino group described in JP-A-1-165613 can also be used suitably.

In addition, the aforementioned ester monomers can be used as a mixture.

Illustrative examples of the amide monomers of aliphatic polyhydric amine compounds with unsaturated carboxylic acids include methylenebis-acrylamide, methylenebis-methacrylamide, 1,6-hexamethylenebis-acrylamide, 1,6-hexamethylenebis-methacrylamide, diethylenetriaminetrisacrylamide, xylylenebisacrylamide and xylylenebismethacrylamide.

As another preferred amide based monomers, the compounds having cyclohexylene structure described in JP-B-54-21726 can be cited.

Also suitable is a urethane based addition-polymerizable compound which is produced using the addition reaction of isocyanate with hydroxyl group, and its illustrative examples include a vinyl urethane compound described in JP-B-48-41708, which contains two or more polymerizable vinyl groups in one molecule and is produced by adding a hydroxyl group-containing vinyl monomer represented by the following formula (V) to a polyisocyanate compound having two or more isocyanate groups in one molecule.

$$CH_2=C(R)COOCH_2CH(R')OH \quad (V)$$

(In this formula, each of R and R' represents H or $CH_3$.)

Also preferred are urethane acrylates described in JP-A-51-37193, JP-B-2-32293 and JP-B-2-16765 and urethane compounds having ethylene oxide based nucleus described in JP-B-58-49860, JP-B-56-17654, JP-B-62-39417 and JP-B-62-39418.

In addition, a photopolymerizable composition having markedly excellent sensitizing speed can be obtained by the use of addition-polymerizable compounds having amino structure or sulfide structure in one molecule, described in JP-A-63-277653, JP-A-63-260909 and JP-A-1-105238.

Other examples include multifunctional acrylates and methacrylates such as polyester acrylates and epoxy acrylates obtained by allowing an epoxy resin to react with (meth) acrylic acid, described in JP-A-48-64183, JP-B-49-43191 and JP-B-52-30490. The specified unsaturated compounds described in JP-B-46-43946, JP-B-1-40337 and JP-B-1-40336 and the vinyl phosphonate based compounds described in JP-A-2-25493 can also be exemplified. In some cases, the structure containing a perfluoroalkyl group as described in JP-A-61-22048 can be used suitably. Also useful are compounds described as photo-curable monomer and oligomer in *Journal of the Adhesion Society of Japan*, Vol. 20, No. 7, pp. 300–308 (1984).

Details of the use of these addition-polymerizable compounds, such as selection of the structure, single use or joint use and amount to be added, can be optionally set corresponding to the performance designing of final sensitive material. For example, they are selected from the following viewpoints. From the viewpoint of sensitizing speed, a structure having larger unsaturated group content in one molecule is desirable, and two or more functional groups are desirable in most cases. Also, three or more functional groups are desirable for the purpose of increasing strength of an imaging part, namely the hardening coat, and joint use of a compound having different functional number and different polymerizable group (e.g., an acrylic ester, a methacrylic ester, a styrene compound or a vinyl ether compound) is an effective method for regulating both photosensitivity and strength. A compound having large molecular weight or high hydrophobic property is excellent in sensitizing speed and film strength, but is not desirable in some cases in terms of developingspeedandprecipitationin the developingsolution. Also, selection and use method of the addition polymerization compound are important factors for the miscibility with and dispersibility of other components in the photosensitive layer (e.g., binder polymer, initiator and colorant); for example, the miscibility is improved in some cases by the use of a low purity compound or two or more compound. In addition, it is possible to select a specific structure for the purpose of improving adhesive property of the support or overcoat layer. Regarding formulation ratio of the addition-polymerizable compound in the photosensitive layer, larger ratio is advantageous from the viewpoint of sensitivity, but too larger ratio may cause problems such as undesirable phase separation, production step-related problems caused by adhesive property of the photosensitive layer (e.g., production failure due to transfer and adhesion of photosensitive material components) and generation of precipitate from the developing solution. In view of these points, desirable formulation ratio is in most cases from 5 to 80% by weight, preferably from 25 to 75% by weight, based on the total component of the composition. Also, these compounds may be used alone or as a mixture of two or more. Regarding use method of the addition-polymerizable compound, appropriate structure, formulation and amount to be added can be optionally selected from the viewpoints of the degree of polymerization inhibition for oxygen, resolution, fogging, changes in refraction index, surface adhesive property-and the like factors, and layer constitution and coating method, such as under coating and over coating, can also be carried out as occasion demands.

(B2) Binder polymer

In applying to lithographic printing plates as a preferred embodiment of the present invention, it is desirable to use a binder polymer in the photosensitive layer. As the binder, it is preferable to contain a linear organic high molecular polymer. Such a "linear organic high molecular polymer" is not particularly limited. Preferably, a linear organic high molecular polymer capable of dissolving or swelling in water or weak alkali aqueous solution is selected, because it renders possible water development or weak alkali aqueous solution development. The linear organic high molecular polymer is selected and used not only as a film forming agent of the composition but also depending on its use as a water, weak alkali aqueous solution or organic solvent developing agent. For example, water development becomes possible when a water-soluble organic high molecular polymer is used. Examples of such a linear organic high molecular polymer include addition polymers having carboxylate groups on their side chains, described for example in JP-A-59-44615, JP-B-54-34327, JP-B-58-12577, JP-B-54-25957, JP-A-54-92723, JP-A-59-53836 and JP-A-59-71048, such as a methacrylic acid copolymer, an acrylic acid copolymer, an itaconic acid copolymer, a crotonic acid copolymer, a maleic acid copolymer and a partially esterificated maleic acid copolymer. There are acidic cellulose derivatives also having carboxylate groups on their side chains in the same manner. In addition to these compounds, those in which cyclic acid anhydrides are added to addition polymers having hydroxyl group are also useful.

Among these compounds, [benzyl (meth)acrylate/(meth) acrylic acid/other addition-polymerizable vinyl monomer as occasion demands] copolymers and [allyl (meth)acrylate/ (meth)acrylic acid/other addition-polymerizable vinyl monomer as occasion demands] copolymers are desirable, because they are well-balanced in terms of film strength, sensitivity and developing property.

Also, the acid group-containing urethane based binder polymers described for example in JP-B-7-12004, JP-B-7-120041, JP-B-7-120042, JP-B-8-12424, JP-A-63-287944, JP-A-63-287947, JP-A-1-271741 and Japanese Patent Application No. 10-116232 have markedly excellent strength, so that they are advantageous in terms of printing durability and low exposure fitness.

The amido group-containing binder described in JP-A-11-171909 is also desirable, because it has both excellent developing property and film strength.

In addition to these binders, polyvinyl pyrrolidone, polyethylene oxide and the like are useful as water-soluble linear organic high polymers. An alcohol-soluble nylon and a polyether of 2,2-bis-(4-hydroxyphenyl)-propane with epichlorohydrin are also useful for the purpose of increasing strength of hardened film. These linear organic high molecular polymers can be contained in the total composition in an optional amount. However, the amount if exceeding 90% by weight would bear no desirable effect in terms, for example, of image strength. Preferred is from 30 to 85% by weight. Also, it is desirable to use the photopolymerizable compound having ethylenic unsaturated double bond and the linear organic high molecular polymer within the range of from 1/9 to 7/3 as weight ratio. In a preferred embodiment, a binder polymer which is substantially insoluble in waterandsolublein alkalinesolution isused. Byusingsuch abinder, an organic solvent undesirable as developing solution from the environmental point of view can be avoided or limited to a considerably small amount. In such a use method, acid value (the acid content per 1 g polymer, expressed by the chemical equivalent number) and molecular weight of the binder polymer are optionally selected in view of image strength and developing property. Preferred acid value is from 0.4 to 3.0 meq/g, and preferred-molecular weight is within the range of from 3,000 to 500,000 in terms of a weight-average molecular weight, more preferably, the acid value is from 0.6 to 2.0 and the molecular weight is within the range of from 10,000 to 300,000.

[C. Other components]

Other components suited for the use and production method can be optionally added to the photosensitive layer of the present invention. Preferred additives are exemplified in the following.

(C1) Co-sensitizer

The sensitivity can be further improved by the use of a certain additive (to be referred to as "co-sensitizer" hereinafter). The action mechanism is not clear but considered to be based, mostly, on the following chemical process. That is, it is assumed that new active radicals are formed by the reaction of a co-sensitizer with various intermediate active species (e.g., radicals, peroxides, oxidants and reductants) which are formed during the steps of the photoreaction initiated by light absorption of the aforementioned initiation system and the subsequent addition polymerization reaction. These compounds are roughly classified into (a) those which produce active radicals by undergoing reduction, (b) those which produce active radicals by undergoing oxidation and (c) those which react with radicals having low activity to convert them into more highly active radicals or act as a chain transfer agent, though there are many cases having no popular views regarding which compound belongs to which of these types.

(a) Compounds which produce active radicals by undergoing reduction

Compound having carbon-halogen bond: considered to generate active radicals by reductive cleavage of carbon-halogen bond. As illustrative examples, trihalomethyl-s-triazines and trihalomethyloxadiazoles can be suitably used.

Compound having nitrogen-nitrogen bond: considered to generate active radicals by reductive cleavage of nitrogen-nitrogen bond. As illustrative examples, hexaarylbiimidazoles are suitably used.

Compound having oxygen-oxygen bond: considered to generate active radicals by reductive cleavage of oxygen-oxygen bond. As illustrative examples, organic peroxides are suitably used.

Onium compound: considered to generate active radicals by reductive cleavage of carbon-hetero bond or oxygen-nitrogen bond. Its useful illustrative examples include diaryliodonium salts, triarylsulfonium salts and N-alkoxypyridinium (azinium) salts.

Ferrocene and iron allene complexes: active radicals can be produced reductively.

(b) Compound which produces active radicals by undergoing oxidation

Alkylate complex: considered to form active radicals by oxidative cleavage of carbon-hetero bond. Illustratively, triaryl alkylborates are suitably used.

Alkylamine compound: considered to form active radicals by oxidative cleavage of C—X bond on the carbon adjacent to nitrogen. Preferred examples of X include hydrogen atom, carboxyl group, trimethylsilyl group and benzyl group. Illustratively, ethanolamines, N-phenylglycines and N-trimethylsilylmethylanilines can be exemplified.

Sulfur- or tin-containing compound: a compound in which nitrogen atom of the aforementioned amines is replaced by sulfur or tin atom can form active radicals by the same action. Also, it is known that a compound having S—S bond can effect sensitization by S—S cleavage.

α-Substituted methylcarbonyl compound: active radicals can be formed by oxidative cleavage of carbonyl-α carbon bond. Similar compound in which carbonyl is converted into oxime ether also shows the same action. Illustrative examples include 2-alkyl-1-[4-(alkylthio)phenyl]-2-morpholinopulonone-1 compounds and oxime ethers obtained by allowing these compounds to react with hydroxyamines and then carrying out etherification of N—OH.

Sulfinic acid salts: active radicals can be formed reductively. Illustratively, sodium arylsulfinate can be exemplified.

(c) Compound which reacts with radicals to convert them into more highly active radicals or acts as a chain transfer agent: for example, compounds having SH, PH, SiH or GeH in the molecule can be used. These compounds form radicals by donating hydrogen to low activity radical species or can form radicals by removing proton after oxidation. Its illustrative examples include 2-mercaptobenzimidazoles.

A large number of illustrative examples of these co-sensitizers are described for example in JP-A-9-236913 as additives for the purpose of improving sensitivity. Some of them are exemplified in the following, though the present invention is not restricted thereby. The symbol -TMS represents trimethylsilyl group.

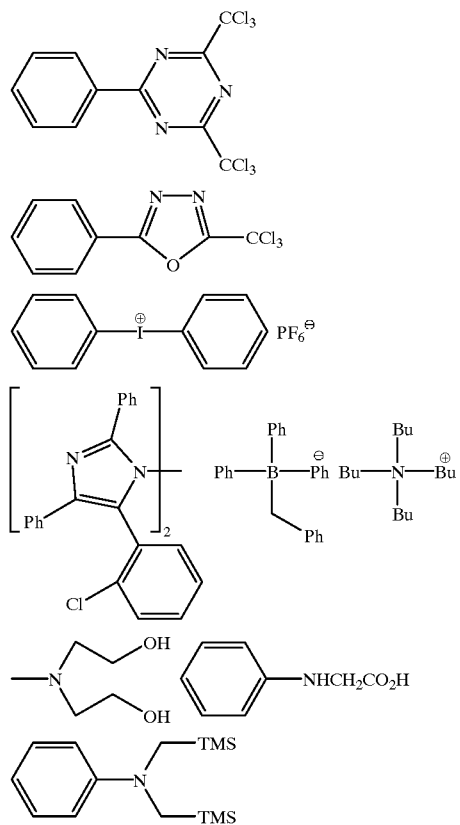

-continued

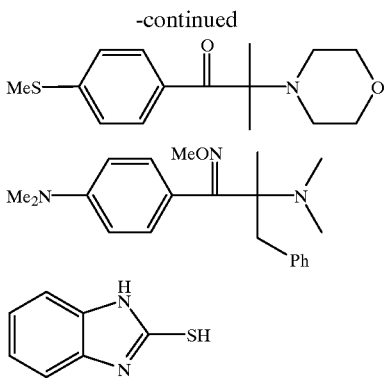

Regarding these co-sensitizers, it is possible to carry out various chemical modifications for the purpose of improving characteristics of the photosensitive layer, similar to the case of the aforementioned sensitizing dyes. For example, various methods can be employed, such as their binding to the sensitizing dyes, activators, addition-polymerizable unsaturated compounds and other parts, introduction of hydrophilic moiety, improvement of miscibility and introduction of substituent groups for inhibiting crystallization or for improving adhesion, as well as their polymerization.

These co-sensitizers can be used alone or as a mixture of two or more. They are used in an amount of from 0.05 to 100 parts by weight, preferably from 1 to 80 parts by weight, more preferably from 3 to 50 parts by weight, based on 100 parts by weight of the compound having ethylenic unsaturated double bond.

(C2) Polymerization inhibitor

According to the present invention, in order to prevent unnecessary heat polymerization of the polymerizable compound having ethylenic unsaturated double bond during production or preservation of the photosensitive composition, it is desirable to add a small amount of a heat polymerization inhibitor in addition to the aforementioned basic components. Examples of suitable heat polymerization inhibitors include hydroquinone, p-methoxyphenol, di-t-butyl-p-cresol, pyrogallol, t-butylcatechol, benzoquinone, 4,4'-thiobis(3-methyl-6-t-butylphenol), 2,2'-methylenebis(4-methyl-6-t-butylphenol) and N-nitrosophenylhydroxyamine cerium(III) salt. Amount of the heat polymerization inhibitor to be added is preferably from about 0.01% by weight to about 5% by weight, based on the weight of total composition. As occasion demands, in order to prevent polymerization inhibition by oxygen, a higher fatty acid derivative such as behenic acid or behenic acid amide may be added and localized on the photosensitive layer surface during the drying step after coating. Amount of the higher fatty acid derivative to be added is preferably from about 0.5% by weight to about 10% by weight, based on the total composition.

(C3) Colorant and the like

Also, a dye or pigment maybe added for the purpose of coloring the photosensitive layer. Addition of such an agent renders possible improvement of so-called suitability for plate inspection, such as visibility after plate-making and fitness to an image density analyzer. Since many dyes cause reduced sensitivity of the photosensitive layer, it is particularly desirable to use a pigment as the coloring agent. Illustrative examples include pigments such as a phthalocyanine pigment, an azo pigment, carbon black and titanium oxide and dyes such as Ethyl Violet, Crystal Violet, an azo dye, an anthraquinone dye and a cyanine dye. The dye and pigment are added in an amount of preferably from about 0.5% by weight to about 5% by weight based on the total composition.

(C4) Other additives

In addition, other known additive agents may also be added, such as an inorganic filler and a plasticizer for improving physical properties of hardened film and a desensitizer which can improve inking property of the photosensitive layer surface.

Examples of the plasticizer include dioctyl phthalate, didodecyl phthalate, triethylene glycol dicaprylate, dimethyl glycol phthalate, tricresyl phosphate, dioctyl adipate, dibutyl sebacate and triacetylglycerol, and, when a binder is used, it can be added in an amount of 10% by weight or less based on the total weight of the compound having ethylenic unsaturated double bond and the binder.

A UV initiator and a heat crosslinking agent can also be added for reinforcing effects of heating and exposure after development, with the aim of improving film strength (printing durability) which will be described later.

In addition to the above, it is possible to add an additive or arrange an intermediate layer, for the purpose of improving adhesion between the photosensitive layer and a support or increasing removing property of unexposed photosensitive layer at developing stage. For example, the adhesive property is improved and the printing durability can be increased by the addition or undercoating of a compound which shows relatively strong interaction with the base plate, such as a compound having diazonium structure or a phosphone compound, and developing ability of non-image part is improved and anti-scumming property can be improved by the addition or undercoating of a hydrophilic polymer such as polyacrylic acid or polysulfonic acid.

When the photopolymerizable composition of the present invention is coated on a support, it is used by dissolving in various organic solvents. Examples of the solvent to be used include acetone, methyl ethyl ketone, cyclohexane, ethyl acetate, ethylene dichloride, tetrahydrofuran, toluene, ethylene glycol monomethyl ether, ethylene glycol monoethyl ether, ethylene glycol dimethyl ether, propylene glycol monoethyl ether, propylene glycol dimethyl ether, acetylacetone, cyclohexanone, diacetone alcohol, ethylene glycol monomethyl ether acetate, ethylene glycol ethyl ether acetate, ethylene glycol monoisopropyl ether, ethylene glycol monobutyl ether acetate, 3-methoxypropanol, methoxymethoxyethanol, diethylene glycol monomethyl ether, diethylene glycol monoethyl ether, diethylene glycol dimethyl ether, diethylene glycol diethyl ether, propylene glycol monomethyl ether acetate, propylene glycol monoethyl ether acetate, 3-methoxypropyl acetate, N,N-dimethylformamide, dimethyl sulfoxide, γ-butyrolactone, methyl lactate and ethyl lactate. These solvents can be used alone or as a mixture. Concentration of solid components in the coating solution is preferably from 2 to 50% by weight.

Since support-coating amount of the photosensitive layer can exert influences mainly upon sensitivity and developing property of the photosensitive layer and strength and printing durability of the exposure film, it is desirable to optionally select the amount depending on each purpose. The coating amount if too small would bear no sufficient printing durability. On the other hand, the amount if too large would cause reduced sensitivity, thus requiring not only an extended time for exposure but also a more prolonged period of time for processing. For a lithographic printing plate for scanning exposure use, which is a main object of the present invention, the coating amount is preferably from about 0.1 g/m$^2$ to about 10 g/m$^2$ as the weight after drying. More preferably, it is from 0.5 to 5 g/m$^2$.

[Support]

In order to obtain a lithographic printing plate as a main object of the present invention, it is desirable to provide the aforementioned photosensitive layer on a support having hydrophilic surface. As the hydrophilic support, any one of the well-known hydrophilic supports used in lithographic printing plates can be used without limitation. Preferably, the support to be used is a plate-like material having dimensional stability, such as paper, paper on which a plastic compound (e.g., polyethylene, polypropylene or polystyrene) is laminated, metal plates (e.g., aluminum, zinc and copper), plastic films (e.g., cellulose diacetate, cellulose triacetate, cellulose propionate, cellulose butyrate, cellulose acetate butyrate, cellulose nitrate, polyethylene terephthalate, polyethylene, polystyrene, polypropylene, polycarbonate and polyvinyl acetal) and paper or plastic films on which the aforementioned metals are laminated or deposited, and, as occasion demands, hydrophilic property may be added to the surface of these supports or they may be subjected to an appropriate well-known physical or chemical treatment for the purpose, for example, of improving their strength.

Among these supports, paper, a polyester film or an aluminum plate are preferred, and the aluminum plate is particularly preferred, because it has good dimensional stability, is relatively inexpensive and can provide a surface having excellent hydrophilic property and strength by a surface treatment as occasion demands. Also preferred is the complex sheet described in JP-B-48-18327, in which an aluminum sheet is bonded onto a polyethylene terephthalate film.

Desirable aluminum plate is a pure aluminum plate or an alloy plate which contains aluminum as the main component and hetero-elements in trace amounts, or it may be a plastic film on which aluminum is laminated or deposited. Examples of the hetero-elements contained in the aluminum alloy include silicon, iron, manganese, copper, magnesium, chromium, zinc, bismuth, nickel and titanium. The hetero-element content of the alloy. is merely 10% by weight or less. Though the particularly desirable aluminum to be used in the present invention is pure aluminum, it is difficult to produce perfectly pure aluminum from the viewpoint of refining techniques, so that it may contain trace amounts of hetero-elements. Regarding such an aluminum plate to be applied to the present invention, its composition is not specified, and any aluminum plate of well known and generally used material can be used at will. The aluminum plate to be used in the present invention may have a thickness of from about 0.1 mm to about 0.6 mm, preferably from 0.15 mm to 0.4 mm, more preferably from 0.2 mm to 0.3 mm.

In the case of a support having a metal, particularly aluminum, surface, it is desirable to carry out a surface treatment such as surface roughening (graining), soaking in a sodium silicate, potassium fluorozirconate or phosphate aqueous solution or anodizing.

Roughening of the aluminum plate surface can be carried out by various methods, such as a method in which the surface is mechanically roughened, a method in which the surface is electrochemically dissolved and roughened and a method in which the surface is selectively dissolved chemically. As the mechanical method, known methods such as ball grinding, brushing, blast grinding and buffing can be used. Regarding the electrochemical surface roughing method, there is a method in which it is carried out in an electrolytic solution such as of hydrochloric acid or nitric acid by alternating current or direct current. A method in which both currents are combined, as disclosed in JP-A-54-63902, can also be used. Also, in order to remove rolling oil from the surface, degreasing with a surface active agent, an organic solvent or an alkaline aqueous solution is carried out prior to the roughening of aluminum plate as occasion demands.

Also, an aluminum plate which is roughened and then subjected to soaking in sodium silicate aqueous solution is suitably used. As described in JP-B-47-5125, an aluminum plate which is subjected to anodizing treatment and then to soaking treatment in aqueous solution of an alkali metal silicate can be used desirably. The anodizing treatment is carried out by applying a current using the aluminum plate as anode, in an aqueous or non-aqueous electrolytic solution of an inorganic acid such as phosphoric acid, chromic acid, sulfuric acid or boric acid or an organic acid such as oxalic acid or sulfamic acid, or a salt thereof, alone or in a combination of two or more solutions.

Also effective is the silicate electrodeposition method described in U.S. Pat. No. 3,658,662.

Also useful is a surface treatment in which a support treated by electrolytic graining, as disclosed in JP-B-46-27481, JP-A-52-58602 and JP-A-52-30503, is combined with the aforementioned anodizing treatment and sodium silicate treatment.

Also desirable is the method disclosed in JP-A-56-28893, in which a mechanical roughening, a chemical etching, an electrolytic graining, an anodizing treatment and a sodium silicate treatment are carried out in that order.

Also desirable is a method in which a plate after completion of these treatments is further undercoated with a water-soluble resin such as polyvinyl phosphonate or a polymer or copolymer having sulfonate group side chains, polyacrylic acid, a water-soluble metal salt (e.g., zinc borate), a yellow dye or an amine salt.

In addition, a sol-gel-treated plate prepared by covalent bonding of a functional group capable of generating addition reaction by radicals, as disclosed in JP-A-7-159983, can also be used desirably.

A method in which a water-resistant hydrophilic layer is arranged as a surface layer on an optional support can also be cited as another preferred example. Examples of such a surface layer include the layer comprising an inorganic pigment and a binder described for example in U.S. Pat. No. 3,055,295 and JP-A-56-13168, the hydrophilic swelling layer described in JP-A-9-80744 and the sol-gel film described in JP-W-8-507727 (the term "JP-W" as used herein means an "unexamined published Japanese international patent application"), which comprises titanium oxide, polyvinyl alcohol and silicic acids.

These hydrophilic treatments are carried out not only to give hydrophilic property to the support surface but also to prevent undesirable reactions of the photopolymerizable composition to be arranged thereon and to improve adhesive property of the photosensitive layer.

[Protective layer]

According to the lithographic printing plate for scanning exposure use as a desirable embodiment of the present invention, the exposure is generally carried out in the air, so that it is desirable to arrange a protective layer further on the photopolymerizable composition layer. The protective layer renders possible the exposure in the air by preventing contamination of the photosensitive layer with low molecular weight compounds such as oxygen and basic substances, which inhibit the image forming reaction generated by exposure in the photosensitive layer. Accordingly, the characteristics expected from such a protective layer are that it has low permeability of low molecular weight compounds such as oxygen, it does not substantially inhibit permeation of light to be used for exposure, it has excellent adhesive property to the photosensitive layer and it can be easily removed at the developing step after exposure. Such measures regarding the protective layer have been made in the prior art and are described in detail in U.S. Pat. No. 3,458,311 and JP-A-55-49729. Regarding the materials which can be used in the protective layer, it is desirable to use water-soluble polymer compounds having relatively excellent crystallinity, and their known illustrative examples include water-soluble polymers such as polyvinyl alcohol, polyvinyl pyrrolidone, acidic celluloses, gelatin, gum arabic and polyacrylic acid, in which the use of polyvinyl alcohol as the main component gives most excellent results of basic characteristics such as oxygen blocking ability and removable property at developing stage. The polyvinyl alcohol to be used in the protective layer may be substituted partially with an ester, an ether and an acetal, with the proviso that it contains unsubstituted vinyl alcohol units for keeping necessary oxygen blocking ability and water-solubility. In the same manner, a part of it may have other copolymer component. Examples of the polyvinyl alcohol include those which are hydrolyzed at a ratio of from 71 to 100 mol % and have a weight-average molecular weight of from 300 to 2,400. Their illustrative examples include those which are manufactured by KURARAY CO., LTD. such as PVA-105, PVA-110, PVA-117, PVA-117H, PVA-120, PVA-124, PVA-124H, PVA-CS, PVA-CST, PVA-HC, PVA-203, PVA-204, PVA-205, PVA-210, PVA-217, PVA-220, PVA-224, PVA-217EE, PVA-217E, PVA-220E, PVA-224E, PVA-405, PVA-420, PVA-613 and L-8.

Components (selection of PVA and use of additive agents), coating amount and the like conditions of the protective layer are selected by taking into consideration its oxygen blocking ability and removal property at developing stage, as well as fogging, adhesive property and scratch resistance. In general, the oxygen blocking ability becomes high as the hydrolyzing ratio of PVA becomes high (as the ratio of unsubstituted vinyl alcohol unit in the protective layer becomes high) and as the coat thickness becomes thick, which is advantageous from the viewpoint of sensitivity. However, when the oxygen blocking ability is increased to an extreme degree, it causes problems such as generation of unnecessary polymerization reaction at the time of production and intact preservation and formation of undesirable fogging and thickening of image lines at the time of image exposure. Also, its adhesion to the image part and scratch resistance are important factors in view of the handling of the plate. That is, when a hydrophilic layer comprised of a water-soluble polymer is laminated on a lipophilic polymerization layer, delamination is apt to occur due to poor adhesive property and the de-laminated region generates a defect such as insufficient coat hardening due to polymerization inhibition by oxygen. Accordingly, various means for improving adhesive property between these two layers have been proposed. For example, JP-A-49-79702 and JP-A-47-469 describe that sufficient adhesive property can be obtained when a hydrophilic polymer mainly comprised of polyvinyl alcohol is mixed with from 20 to 60% by weight of an acrylic emulsion or a water-insoluble vinyl pyrrolidone-vinyl acetate copolymer, and the mixture is laminated on a polymerization layer. Any of such known techniques can be applied to the protective layer of the present invention. These protective layer coating methods are minutely described for example in U.S. Pat. No. 3,458, 311 and JP-A-55-49729.

In addition, other functions can be added to the protective layer. For example, safe light aptitude can be further improved without causing sensitivity reduction, by the addition of a colorant (e.g., a water-soluble dye) which has excellent permeability of an exposing light of from 350 nm to 450 nm and can efficiently absorb lights of 500 nm or more.

When a photosensitive material prepared using the photopolymerizable composition of the present invention is used as an image forming material, an image is generally obtained by carrying out image exposure and then removing un-exposed part of the photosensitive layer by a developing solution. Examples of desirable developing solution in using such photopolymerizable composition for preparing a lithographic printing plate include those which are described in JP-B-57-7427, particularly an aqueous solution of an inorganic alkali agent such as sodium silicate, potassium silicate, sodium hydroxide, potassium hydroxide, lithium hydroxide, sodium tertiary phosphate, sodium secondary phosphate, ammonium tertiary phosphate, ammonium secondary phosphate, sodium metasilicate, sodium bicarbonate or aqueous ammonia or an organic alkali agent such as monoethanolamine or diethanolamine. Such an alkali solution is added to a concentration of from 0.1 to 10% by weight, preferably from 0.5 to 5% by weight.

As occasion demands, such an alkaline aqueous solution can contain small amounts of a surface active agent and an organic solvent Isuch as benzyl alcohol, 2-phenoxyethanol or 2-butoxyethanol. Their examples include those which are described in U.S. Pat. No. 3,375,171 and U.S. Pat. No. 3,615,480.

Also excellent are those developing solutions which are described in JP-A-50-26601, JP-A-58-54341, JP-B-56-39464 and JP-B-56-42860.

As another plate-making process of the lithographic printing plate precursor of the present invention, whole heating may be carried out before exposure, during exposure or during a period between exposure and development as occasion demands. Such a heating accelerates image forming reaction in the photosensitive layer and bears advantages such as improvement of sensitivity and printing durability and stabilization of sensitivity. Also it is effective to carry out whole after-heating or whole exposure of the image after development, for the purpose of improving image strength and printing durability. In general, it is desirable to carry out the heating before development under a mild condition of 150° C. or less. The temperature if too high would cause problems such as fogging of even the non-image part. An extremely strong condition is applied to the heating after development. It is generally within the range of from 200 to 500° C. The temperature if too low would bear no sufficient image strengthening action and if too high would cause problems such as deterioration of the support and thermal decomposition of the image part.

Regarding exposure method of the scanning exposure lithographic printing plate of the present invention, any of the known methods can be used without limitation. Desirable wavelength of the light source is from 350 nm to 450 nm, and, illustratively, an InGaN semiconductor laser is desirable. The exposure mechanism may be any of internal drum system, external drum system and flat bed system. In addition, the photosensitive layer components of the present invention can be made soluble in neutral water and weakly alkaline aqueous solution by the use of components having high water solubility, and a lithographic printing plate of such a construction can be applied a system in which the plate is loaded on a printing machine and then exposure and development are carried out on the machine.

The following can be used as available laser beam sources of 350 to 450 nm.

As a gas laser, Ar ion laser (364 nm, 351 nm, 10 mW–1 W), Kr ion laser (356 nm, 351 nm, 10 mW–1 W) or He—Cd laser (441 nm, 325 nm, 1 mW–100 mW), as a solid laser, a combination of Nd:YAG(YVO$_4$) with SHG crystals×2 (355 nm, 5 mW–1 W) or a combination of Cr:LiSAF with SHG crystals (430 nm, 10 mW), as a semiconductor laser system, a KNBOb ring resonator (430 nm, 30 mW), a combination of a wave guide type wave sensing element with an AlGaAs or InGaAs semiconductor (380 nm–450 nm, 5 mW–100 mW), a combination of a wave guide type wave sensing element with an AlGaInP or AlGaAs semiconductor (300 nm–350 nm, 5 mW–100 mW) or AlGaInN (350 nm–450 rm, 5 mW–30 mW), and as a pulse laser, N$_2$ laser (337 nm, pulse 0.1–10 mJ) or XeF (351 nm, pulse 10–250 mJ).

Among these light sources, the AlGaInN semiconductor laser (commercially available InGaN system semiconductor laser, 400–410 nm, 5–30 mW) is particularly suitable in terms of wavelength characteristics and cost.

Also, the lithographic printing plate exposure apparatus of scanning exposure system is divided into internal drum system, external drum system and flat bed system, and all of the aforementioned light sources, excluding pulse lasers, can be used as the light source. From the practical point of view, the following exposure apparatuses are particularly desirable based on the relationship between photosensitive material sensitivity and plate-making time.

A single beam exposure apparatus of internal drum system, which uses one gas laser or solid laser beam source.

A multi-beam exposure apparatus of flat bed system, which uses a number of semiconductor lasers (10 or more).

A multi-beam exposure apparatus of external drum system, which uses a number of semiconductor lasers (10 or more).

In the aforementioned laser direct imaging lithographic printing plate, the following equation (eq 1) is generally set up among photosensitive material sensitivity X (J/cm$^2$), exposure area of photosensitive material S (cm$^2$), power of one laser beam source q (W), the number of lasers n and total exposure time t (s).

$$X \cdot S = n \cdot q \cdot t \quad (eq\ 1)$$

i) In the case of internal drum (single beam) system, the following equation (eq 2) is generally set up among laser revolution speed f (radian/s), sub-scanning length of photosensitive material Lx (cm), resolution Z (dot/cm) and total exposure time t (s).

$$f \cdot Z \cdot t = Lx \quad (eq\ 2)$$

ii) In the case of external drum (multi-beam) system, the following equation (eq 3) is generally set up among drum revolution speed F (radian/s), sub-scanning length of photosensitive material Lx (cm), resolution Z (dot/cm), total exposure time t (s) and the number of beams (n).

$$F \cdot Z \cdot n \cdot t = Lx \quad (eq\ 3)$$

iii) In the case of flat bed (multi-beam) system, the following equation (eq 4) is generally set up among polygon mirror revolution speed H (radian/s), sub-scanning length of photosensitive material Lx (cm), resolution Z (dot/cm), total exposure time t (s) and the number of beams (n).

$$H \cdot Z \cdot n \cdot t = Lx \quad (eq\ 4)$$

When the resolution required for practical printing plate (2,560 dpi), the plate size (A1/B1, sub-scanning length 42 inch), the exposure condition of about 20 sheets/1 hour and the photosensitive characteristics (photosensitive wavelength, sensitivity: about 0.1 mJ/cm$^2$) of the photosensitive composition of the present invention are substituted for the above equations, it can be understood that a combination with a semiconductor laser multi-beam exposure system is more desirable for the photosensitive material of the present invention. In addition, when other factors such as workability and cost are included, it can be understood that a combination with the external drum system semiconductor laser multi-beam exposure system is most desirable.

In addition, other exposure lights such as an ultra-high pressure, highpressure, mediumpressureorlowpressuremercurylamp, a chemical lamp, a carbon arc lamp, a xenon lamp, a metal halide lamp, various types of visible and ultraviolet laser lamps, a fluorescent lamp, a tungsten lamp and the sunlight can also be applied to the photopolymerizable composition of the present invention. Regarding the use of the photopolymerizable composition of the present invention, it can be applied not only to lithographic printing plates for scanning exposure use but also to various other materials known as the use of photo-curing resins without limitation. For example, a highly sensitive material for optical image formation can be obtained by applying it to a liquid photopolymerizable composition with joint use of a cation-polymerizable compound as occasion demands. Also, it can be made into a hologrammaterial making use of its changes in refraction index accompanied by its photopolymerization. It can also be applied to various transfer materials (e.g., peeling photosensitive material and toner development sensitive material) making use of its changes in surface adhesive property accompanied by photopolymerization. Also, it can be applied to photo-curing of microcapsules. It can also be applied to the production of electronic materials such as photo-resists and photo-curing resin materials such as inks, paints and adhesives.

EXAMPLES

Examples of the present invention are given below by way of illustration and not by way of limitation.

Synthesis Example 1

Synthesis of 2-(1-methylnaphtho[1,2-d]thiazol-2 (1H)-ylidene)-1,3-dihydro-1-oxo-2H-indene (D1)

A flask was charged with 19.4 ml (25.2 mmol) of diisopropylamine and 150 ml of THF to which, while ice-cooling in a stream of nitrogen, was then gradually added dropwise 1.3 N hexane solution of n-butyl lithium. After 30 minutes of stirring, the ice bath was changed to a dry ice/ethanol bath, and a solution prepared by dissolving 3.17 g (24.0 mmol) of 1-indanone in 50 ml of THF was slowly added dropwise. After additional 1 hour of stirring, to this was added 5 g (12.0 mmol) of 1-methyl-2-(methylthio)-naphtho[1,2-d]thiazolium 4-methylbenzenesulfonate powder in small portions. After additional 3 hours of stirring, the reaction solution was gradually returned to room temperature and then the reaction was completed by adding water to the reaction solution. The reaction solution was acidified with dilute hydrochloric acid and extracted with ethyl acetate, the thus obtained oil layer was washed with water and dried with magnesium sulfate, and then the solvent was evaporated under a reduced pressure to obtain black and oily crude product. By carrying out purification with a silica gel column chromatography using ethyl acetate/methylene chloride (15:85 v:v) as the eluent, 1.2 g (3.64 mmol) of yellow crystals of D1 was obtained. Yield was 30%. Its structure was identified by nuclear magnetic resonance spectrum, infrared absorption spectrum, mass spectrometry spectrum and elemental analysis (found; carbon 76.59%, hydrogen 14.57% calcd.; carbon 76.57%, hydrogen 4.59%).

Melting point [230–245° C.] ($CHCl_3$-EtOAc), electron absorption spectrum (THF): absorption maximum wavelength 421 nm, absorption maximum molar absorbance coefficient 48000.

Synthesis Example 2

Synthesis of 2-(3-ethyl-2(3H)-benzothiazolylidene)-1,3-dihydro-1-oxo-2H-indene (D2)

A flask was charged with 6.12 g (153 mmol) of sodium hydride (60 wt %), and 500 ml of THF was added thereto in a stream of nitrogen and stirred to make a suspension. While ice-cooling, to this was added 30 g (76.3 mmol) of 3-ethyl-2-(ethylthio)-2(3H)-benzothiazolium 4-methylbenzenesulfonate powder in small portions. Next, to this was added dropwise 100 ml of THF solution containing 20.2 g (153 mmol) of 1-indanone. The reaction solution was stirred under ice-cooling for 3 hours and at room temperature for 3 hours and then mixed with 20 ml of methanol. When the reaction solution was poured in small portions into a stirred mixed solution of 1 liter of water and 1 liter of methanol, yellow crude crystals were obtained. The crude crystals were suspended in 200 ml of methanol, refluxed, purified and then collected by filtration, thereby obtaining 7.06 g (24.1 mmol) of ocherous crystals of D2. Yield was 32%. Its structure was identified by nuclear magnetic resonance spectrum, infrared absorption spectrum, mass spectrometry spectrum and elemental analysis (found; carbon 73.41%, hydrogen 5.12% calcd., carbon 73.69%, hydrogen 5.15%).

Melting point [205–215° C.] (MeOH), electron absorption spectrum (MeOH): absorption maximum wavelength 411 nm, absorption maximum molar absorbance coefficient 44000. Oxidation potential ($CH_3CN$, vs Ag/AgCl) +0.90 V.

Synthesis Example 3

Synthesis of 2-(3-ethyl-2(3H)-benzothiazolylidene)-1,3-dihydro-1-oxo-3-phenyl-2H-indene (D14)

A flask was charged with 1.2 g (30 mmol) of sodium hydride (60 wt %), and 100 ml of THF was added thereto in a stream of nitrogen and stirred to make a suspension. While ice-cooling, to this was added 5.9 g (15 mmol) of 3-ethyl-2-(ethylthio)-2(3H)-benzothiazolium 4-methylbenzenesulfonate powder in small portions. Next, to this was added dropwise 50 ml of THF solution containing 6.24 g (30 mmol) of 3-phenyl-1-indanone. The reaction solution was stirred under ice-cooling for 3 hours and at room temperature for 3 hours and then mixed with 20 ml of methanol. When the reaction solution was poured in small portions into a stirred mixed solution of 100 ml of water and 100 ml of methanol, yellow crude crystals were obtained. The crude crystals were suspended in 100 ml of methanol, refluxed, purified and then collected by filtration, thereby obtaining 1.23 g (3.33 mmol) of yellow crystals of D14. Yield was 22%. Its structure was identified by nuclear magnetic resonance spectrum, infrared absorption spectrum, mass spectrometry spectrum and elemental analysis (found; carbon 78.00%, hydrogen 5.15% calcd.; carbon 78.02%, hydrogen 5.18%).

Melting point [203–205° C.] (MeOH), electron absorption spectrum (MeOH): absorption maximum wavelength 412 nm, absorption maximum molar absorbance coefficient 41000. Oxidation potential ($CH_3CN$, vs Ag/AgCl) +0.95 V.

Synthesis Example 4

Synthesis of 2-(3-ethyl-2(3H)-benzothiazolylidene)-1,3-dihydro-3-oxo-2H-indene-1-carboxylic acid (D4)

A flask was charged with 2.4 g (60 mmol) of sodium hydride (60 wt %), and 100 ml of THF was added thereto in a stream of nitrogen and stirred to make a suspension. While ice-cooling, to this was added 5.9 g (15 mmol) of 3-ethyl-2-(ethylthio)-2(3H)-benzothiazolium 4-methylbenzenesulfonate powder in small portions. Next, to this was added dropwise 30 ml of THF solution containing 5.28 g (30 mmol) of 1-carboxy-3-indanone. The reaction solution was stirred under ice-cooling for 3 hours and at room temperature for 3 hours and then mixed with 20 ml of methanol. When the reaction solution was acidified with hydrochloric acid and poured in small portions into a stirred mixed solution of 100 ml of water and 100 ml of methanol, yellow crude crystals were obtained. The crude crystals were suspended in 100 ml of methanol, refluxed, purified and then collectedby filtration, thereby obtaining 1.48 g (4.39mmol) of yellow crystals of D4. Yield was 29%. Its structure was identified by nuclear magnetic resonance spectrum, infrared absorption spectrum, mass spectrometry spectrum and elemental analysis (found; carbon 67.61%, hydrogen 4.48% calcd.; carbon 67.64%, hydrogen 4.48%). Melting point [163–168° C.] (MeOH)

Synthesis Example 5

Synthesis of 2-(3-(trimethylsilylmethyl)-2(3H)-benzothiazolylidene)-1,3-dihydro-1-oxo-2H-indene (D3)

In a flask, 5.2 g (22 mmol) of trimethylsilylmethyl triflate, 3.63 g (20 mmol) of 2-(methylthio)benzothiazole and 20 ml of methylene chloride were mixed and stirred for 2 hours. After evaporation of methylene chloride under a reduced pressure, the resulting residue was mixed with 100 g of ethyl acetate and the thus precipitated solid was collectedby filtration to obtain 7.7 g (18 mmol) of white crystals of 3-(trimethylsilylmethyl)-2-(methylthio)-2(3H)-benzothiazolium triflate.

Next, a flask was charged with 0. 8 g (20 mol) of sodium hydride (60 wt %), and 100 ml of THF was added thereto in a stream of nitrogen and stirred to make a suspension. While ice-cooling, to this was added 4.18 g (10 mmol) of 3-(trimethylsilylmethyl)-2-(methylthio)-2(3H)-benzothiazolium triflate powder in small portions. Next, to this was added dropwise 100 ml of THF solution containing 2.64 g (20 mmol) of 1-indanone. The reaction solution was stirred under ice-cooling for 3 hours and at room temperature for 3 hours and then mixed with 20 ml of methanol. When the reaction solution was poured in small portions into a stirred mixed solution of 1 liter of water and 1 liter of methanol, yellow crude crystals were obtained. The crude crystals were suspended in 200 ml of methanol, refluxed, purified and then collected by filtration, thereby obtaining 1.2 g (3.41 mmol) of ocherous crystals of D3. Yield was 34%. Its structure was identified by nuclear magnetic resonance spectrum, infrared absorption spectrum, mass spectrometry spectrum and elemental analysis (found; carbon 68.30%, hydrogen 6.05% calcd.; carbon 68.33%, hydrogen 6.02%).

Melting point [188–190° C.] (MeOH), electron absorption spectrum (MeOH): absorption maximum wavelength 417 nm, absorption maximum molar absorbance coefficient 39000. Oxidation potential ($CH_3CN$, vs Ag/AgCl) +0.85 V.

Synthesis Example 6

Synthesis of 2-(5-(1,1-dimethylethyl)-1,3-benzodithiol-2-ylidene)-1,3-dihydro-1-oxo-2H-indene (D18)

A flask was charged with 1.54 g (5 mmol) of 5-(1,1-dimethylethyl)-3a,7a-dihydro-benzodithiol-1-ium perchlorate, 0.33 g (2.5 mmol) of 1-indanone and 10 ml of methylene chloride, and the mixture was stirred at room temperature for 2 hours. After evaporation of methylene chloride under a reduced pressure, the resulting residue was mixed with 20 ml of ethanol, and the thus precipitated crystals were collected by filtration and recrystallized from ethanol to obtain 0.66 g (1.9 mmol) of yellow crystals of D18. Yield was 78%. Its structure was identified by nuclear magnetic resonance spectrum, infrared absorption spectrum, mass spectrometry spectrum and elemental analysis (found; carbon 70.99%, hydrogen 5.39% calcd.; carbon 70.97%, hydrogen 5.36%).

Melting point [210–212° C.] (MeOH), electron absorption spectrum (THF): absorption maximum wavelength 405 nm, absorption maximum molar absorbance coefficient 32000.

Examples 1 to 8 and Comparative Examples 1 to 7
(Preparation of support)

An aluminum plate of 0.3 mm in thickness was soaked 10% by weight sodium hydroxide at 60° C. for 25 seconds to effect etching, washed with running water, neutralized and washed with 20% by weight nitric acid and then washed with water. This was subjected to electrolytic surface roughening treatment in 1% by weight nitric acid aqueous solution using sinusoidal alternating wave form current at an anode electric variable of 300 coulomb/$dm^2$. Subsequently, this was soaked in 1% by weight sodium hydroxide aqueous solution at 40° C. for 5 seconds, soaked again in 30% by weight sulfuric acid aqueous solution to carry out 40 seconds of desmut treatment at 60° C., and then subjected to 2 minutes of anodic oxidation treatment in 20% by weight sulfuric acid aqueous solution at a current density of 2 A/$dm^2$ so that thickness of the anodic oxidation coating became 2.7 g/$m^2$. When measured, its surface roughness was found to be 0.3 μm (Ra expression by JIS B 0601).

The following sol-gel reaction solution was coated on the backside of the thus treated base plate using a bar coater and dried at 100° C. for 1 minute, thereby preparing a support having a back coat layer of 70 mg/$m^2$ in coated amount after drying.

| Sol-gel reaction solution | |
| --- | --- |
| Tetraethyl silicate | 50 parts by weight |
| Water | 20 parts by weight |
| Methanol | 15 parts by weight |
| Phosphoric acid | 0.05 part by weight |

When these components were mixed and stirred, exothermic reaction started after about 5 minutes. After 60 minutes of the reaction, a solution shown in the following was added thereto to prepare a back coat coating solution.

| | |
| --- | --- |
| Pyrogallol formaldehyde condensation resin (molecular weight 2,000) | 4 parts by weight |
| Dimethyl phthalate | 5 parts by weight |
| Fluorine based surface active agent (N-butylperfluorooctane sulfonamide ethylacrylate/polyoxyethylene acrylate copolymer: molecular weight 20,000) | 0.7 part by weight |
| Methanol silica sol (manufactured by Nissan Chemical Industries, methanol 30% by weight) | 50 parts by weight |
| Methanol | 800 parts by weight |

(Preparation of photosensitive layer)

A photopolymerizable composition of the following formulation was coated on the thus treated aluminum plate to a dry base coated amount of from 1.0 to 2.0 g/$m^2$ and dried at 80° C. for 2 minutes to effect formation of a photosensitive layer.

| | |
| --- | --- |
| Pentaerythritol tetraacrylate | 1.5 g |
| Benzyl methacrylate/methacrylic acid copolymer (copolymerization molar ratio 75/25) | 2.0 g |
| Photopolymerization initiation system (see Table 1) | |
| Sensitizing dye (D1, D2, D14, DR-1 to DR-3) | X g |
| Activator (A-1 to A-5) | Y g |
| Co-sensitizer (C-1 to C-3) | Z g |
| Fluorine based nonionic surface active agent (F-177P) | 0.03 g |
| Heat polymerization inhibitor (N-nitrosophenylhydroxylamine aluminum salt) | 0.01 g |
| Pigment dispersion | |
| Composition of pigment dispersion | |
| Composition: Pigment Blue 15:6 | 15 parts by weight |
| Allyl methacrylate/methacrylic acid copolymer (copolymerization molar ratio 83/17) | 10 parts by weight |
| Cyclohexanone | 15 parts by weight |
| Methoxypropyl acetate | 20 parts by weight |
| Propylene glycol monomethyl ether | 40 parts by weight |
| Methyl ethyl ketone | 20 g |
| Propylene glycol monomethyl ether | 20 g |

(Preparation of protective layer)

An aqueous solution of 3% by weight polyvinyl alcohol (saponification value 98 mol %, polymerization degree 550) was coated on the photosensitive layer to a coated dry weight of 2 g/$m^2$ and dried at 100° C. for 2 minutes.

(Evaluation of sensitivity)

Fuji Step Guide (a gray scale in which the permeation optical density changes discontinuously at ΔD=0.15) manufactured by Fuji Photo Film Co., Ltd. was adhered closely onto the thus obtained photosensitive material, and exposure was carried out at known exposure energy using a xenon lamp through an optical filter. Thereafter, development was carried out by soaking the material in a developing solution having the following composition at 25° C. for 10 seconds, and the highest number of steps-at which the image was completely removed was read and its exposure energy level was obtained to calculate the sensitivity (unit, mJ/$cm^2$). Smaller energy level means higher sensitivity. In order to estimate exposure aptitude to short wave semiconductor laser, exposure was carried out with a monochromic light of 400 nm using Kenko BP-40 as the optical filter. The results are shown in Table 1.

(Composition of developing solution)

| | |
|---|---|
| DP-4 (manufactured by Fuji Photo Film Co., Ltd.) | 65.0 g |
| Water | 880.0 g |
| Lipomin LA (20% aqueous solution, mfd. by Lion Corp.) | 50.0 g |

TABLE 1

| | Initiation system | | | | | Photosensitive layer | |
|---|---|---|---|---|---|---|---|
| | Sensitizing Pigment | X (g) | Activator | Y (g) | Co-sensi-tizer | Z (g) | coating amount (mg/m$^2$) | Sensitivity (mJ/cm$^2$) |
| Ex. 1 | D2 | 0.07 | A-1 | 0.06 | — | — | 1.5 | 0.3 |
| Ex. 2 | D2 | 0.07 | A-2 | 0.03 | — | — | 1.5 | 0.2 |
| Ex. 3 | D2 | 0.07 | A-3 | 0.05 | — | — | 1.5 | 0.15 |
| Ex. 4 | D2 | 0.07 | A-4 | 0.08 | C-1 | 0.2 | 1.5 | 0.15 |
| Ex. 5 | D2 | 0.07 | A-5 | 0.1 | C-1 | 0.5 | 1.5 | 0.2 |
| Ex. 6 | D2 | 0.05 | A-2 | 0.06 | C-3 | 0.5 | 1.5 | 0.10 |
| Ex. 7 | D1 | 0.02 | A-1 | 0.05 | C-2 | 0.8 | 2 | 0.25 |
| Ex. 8 | D14 | 0.04 | A-2 | 0.03 | C-2 | 0.6 | 1 | 0.10 |
| Comp. Ex. 1 | D2 | 0.07 | — | — | — | — | 1.5 | >100 |
| Comp. Ex. 2 | — | — | A-1 | — | — | — | 1.5 | >100 |
| Comp. Ex. 3 | — | — | A-2 | 0.03 | — | — | 1.5 | 1.0 |
| Comp. Ex. 4 | — | — | A-4 | 0.08 | C-1 | 0.2 | 1.5 | >100 |
| Comp. Ex. 5 | DR-1 | 0.07 | A-1 | 0.06 | — | — | 1.5 | 0.8 |
| Comp. Ex. 6 | DR-2 | 0.07 | A-1 | 0.06 | — | — | 1.5 | 1.2 |
| Comp. Ex. 7 | DR-3 | 0.07 | A-1 | 0.06 | — | — | 1.5 | 10 |

As is evident from Examples 1 to 8, the initiation system of the present invention shows practically sufficient high sensitivity. It is evident from Comparative Examples 1 to 3 that the initiation system of the present invention can express high sensitivity by the joint use of the sensitizing dye and activator, and it can be understood from Examples 1 to 5 that broad range of compounds can be applied as the activator of the present invention independent of the sensitization mechanism. In addition, comparison of Example 1 with Comparative Examples 5 to 7 suggests that the structural characteristic of the sensitizing dye of the present invention for showing high sensitivity is based on the 1,3-dihydro-1-oxo-2H-indene partial structure, which is an unexpected discovery.

Examples 9 to 16 and Comparative Example 8

Lithographic printing plates were prepared in the following manner and their printing performance was evaluated. The results are shown in Table 2.

[Pretreatment of support]

Using No. 8 nylon brush and water suspension of 800 mesh pumice stone, the surface of an aluminum plate of material 1S having a thickness of 0.3 mm was grained and then thoroughly washed with water. After soaking in 10% by weight sodium hydroxide at 70° C. for 60 seconds to effect etching, the plate was washed with running water, neutralized and washed with 20% by weight nitric acid and then washed with water. This was subjected to electrolytic surface roughening treatment in 1% by weight nitric acid aqueous solution using sinusoidal alternating wave form current at an anode electric variable of 300 coulomb/dm$^2$. When measured, its surface roughness was found to be 0.45 $\mu$m (Ra expression by JIS B 0601).

[Hydrophilic treatment of support surface]

The above-described support was soaked in an aqueous solution of 2.5% by weight No. 3 sodium silicate (SiO$_2$= 28–30%, Na$_2$O=9–10%, Fe=0.02% or less), pH=11.2, at 70° C. for 13 seconds, and then washed with water. The amount of silicate on the surface was calculated to be 10 mg/m$^2$, based on the amount of Si element measured by X-ray fluorescence analysis of the surface.

[Coating of intermediate layer]

A coating solution of the following composition of (A) was prepared, coated on the surface of the thus obtained hydrophilic support using a whirler under a condition of 180 rpm, in such an amount that the amount of coated phenyl phosphonate became 20 mg/m$^2$, and then dried at 80° C. for 30 seconds.

(Intermediate layer coating solution A)

| | |
|---|---|
| Phenyl phosphonate | 0.07 to 1.4 g |
| Methanol | 200 g |

[Coating of photosensitive layer]

A photosensitive solution of the following composition was prepared, coated on the thus intermediate layer-arranged support using a whirler, in such an amount that the coated amount became 1.0 to 2.0 g/m$^2$, and then dried at 100° C. for 1 minute.

(Photosensitive solution)

Addition-polymerizable compound (compound shown in Table 2)

| | |
|---|---|
| Binder polymer (compound shown in Table 2) | 2.0 g |
| Sensitizing dye (compound shown in Table 2) | 0.1 g |
| Activator (compound shown in Table 2) | 0.1 g |
| Co-sensitizer (compound shown in Table 2) | 0.3 g |
| Coloring pigment dispersion | 2.0 g |
| Composition of pigment dispersion | |
| Pigment Blue 15:6 | 15 parts by weight |
| Allyl methacrylate/methacrylic acid copolymer (copolymerization molar ratio 83/17) | 10 parts by weight |
| Cyclohexanone | 15 parts by weight |
| Methoxypropyl acetate | 20 parts by weight |
| Propylene glycol monomethyl ether | 40 parts by weight |
| Heat polymerization inhibitor (N-nitrosophenylhydroxylamine aluminum salt) | 0.01 g |

| | |
|---|---|
| Surface active agent (Megafac F-177, manufactured by Dainippon Ink & Chemicals, Inc.) | 0.02 g |
| Methyl ethyl ketone | 20.0 g |
| Propylene glycol monomethyl ether | 20.0 g |

[Coating of protective layer]

An aqueous solution of 3% by weight polyvinyl alcohol (saponification value 98 mol %, polymerization degree 550) was coated on the photosensitive layer to a coated dry weight of 2 g/m² and dried at 100° C. for 2 minutes.

[Exposure of lithographic printing plate precursor]

The thus obtained lithographic printing plate precursor was subjected to solid image exposure and dot image exposure under conditions of 175 lines/inch and from 1 to 99% dots at 1% intervals, using a monochromatic light of 400 nm and by adjusting the exposure power to a printing plate exposure energy density of 200 μJ/cm².

[Development/plate making]

A lithographic printing plate was obtained by charging an automatic developing machine LP-850 manufactured by Fuji Photo Film Co., Ltd. with a predetermined developing solution (shown in Table 2) and Finisher FP-2W manufactured by Fuji Photo Film Co., Ltd. and then carrying out development/plate making of an exposed plate at a developing solution temperature of 30° C. for a developing time of 18 seconds.

[Printing durability test]

As a printing machine, R 201 manufactured by Roland Co. was used, and GEOS-G (N) manufactured by Dainippon Ink & Chemicals, Inc. was used as the ink. Prints of solid image parts were observed, and the printing durability was examined by the number of prints which started blurring. Larger number means better printing durability.

[Dot printing durability forced test]

As a printing machine, R 201 manufactured by Roland Co. was used, and GEOS-G (N) manufactured by Dainippon Ink & Chemicals, Inc. was used as the ink. The ink of the plate surface after 5,000 times of printing was cleaned by wiping the dotted parts with a sponge for printing use moistened with PS Plate Cleaner CL-2 manufactured by Fuji Photo Film Co., Ltd. Thereafter, the printing was continued for 10,000 times and the plate wearing of dots on the prints was observed with the naked eye.

[Scumming test]

As a printing machine, R 201 manufactured by Roland Co. was used, and GEOS-G (S) manufactured by Dainippon Ink & Chemicals, Inc. was used as the ink. The scumming was evaluated by observing prints of non-image parts (unexposed parts).

(Addition-polymerizable compounds in Table 2)

(M-1)

Pentaerythritol tetraacrylate (NK Ester A-YMMT, manufactured by Shin-Nakamura Chemical Co., Ltd.)

(M-2)

Glycerin dimethacrylate hexamethylene diisocyanate urethane prepolymer (UA101H, manufactured by Kyoei-sha Chemical Co., Ltd.) (Binder polymers in Table 2)

(B-1)

Allyl methacrylate/methacrylic acid/N-isopropylacrylamide (copolymerization molar ratio 67/13/20)

Acid value measured by NaOH titration, 1.15 meq/g

Weight-average molecular weight measured by GPC, 130,000

(B-2)

Allyl methacrylate/methacrylic acid copolymer (copolymerization molar ratio 83/17)

Acid value measured by NaOH titration, 1.55 meq/g

Weight-average molecular weight measured by GPC, 125,000

(B-3)

Polyurethane resin obtained by condensation polymerization of the following diisocyanates and diols.

4,4'-Diphenylmethane diisocyanate (MDI)

Hexamethylene diisocyanate (HMDI)

Polypropylene glycol, weight-average molecular weight 1,000 (PPG 1000)

2,2-Bis(hydroxymethyl)propionic acid (DMPA)

Copolymerization molar ratio (MDI/HMDI/PPG 1000/DMPA) 40/10/15/35

Acid value measured by NaOH titration, 1.05 meq/g

Weight-average molecular weight measured by GPC, 45,000

(Developing solution in Table 2)

(DV-1)

Aqueous solution of pH 10 having the following composition

| | |
|---|---|
| Monoethanolamine | 0.1 part by weight |
| Triethanolamine | 1.5 parts by weight |
| Compound of the following formula 1 | 4.0 parts by weight |
| Compound of the following formula 2 | 2.5 parts by weight |
| Compound of the following formula 3 | 0.2 part by weight |
| Water | 91.7 parts by weight |

(DV-2)

Aqueous solution of pH 10 having the following composition

| | |
|---|---|
| Sodium bicarbonate | 1.2 parts by weight |
| Sodium carbonate | 0.8 part by weight |
| Compound of the following formula 1 | 3.0 parts by weight |
| Compound of the following formula 2 | 2.0 parts by weight |
| Compound of the following formula 3 | 0.2 part by weight |
| Water | 92.8 parts by weight |

(DV-3)

Aqueous solution of pH 13 having the following composition

| | |
|---|---|
| 1 K Potassium silicate | 3.0 parts by weight |
| Potassium hydroxide | 1.5 parts by weight |
| Compound of the following formula 3 | 0.2 part by weight |
| Water | 95.3 parts by weight |

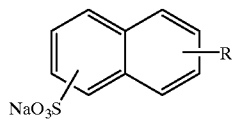

(formula 1)

("Pelex NBL", an anionic surfactant, manufactured by Kao Corporation, wherein R is H or $C_4H_9$.)

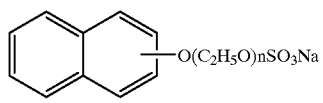

(formula 2)

(A modified product of "Newcol B4", an anionic surfactant, manufactured by Nippon Nyukazai Co., Ltd., wherein n is about 4 (average value).)

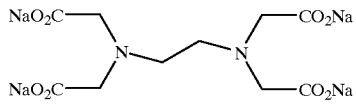

formula 3

TABLE 2

| | Photosensitive layer | | | | | | | Printing performance | | |
|---|---|---|---|---|---|---|---|---|---|---|
| No. | Addition-polymer-izable compound | Binder polymer | Sensitizing dye | Activator | Co-sensitizer | Amount coated (mg/m²) | Developing solution composition | Image part printing durability (sheets) | Dot part printing durability | Anti-scumming of non-image part |
| Ex. 9 | M-1 | B-1 | D3 | A-2 | C-2 | 1.5 | DV-1 | 100,000 | good | good |
| Ex. 10 | M-2 | B-1 | D4 | A-1 | C-2 | 2 | DV-2 | 70,000 | good | good |
| Ex. 11 | M-2 | B-3 | D18 | A-2 | C-1 | 1.8 | DV-3 | 200,000 | good | good |
| Ex. 12 | M-1 | B-2 | D23 | A-2 | C-1 | 2.5 | DV-1 | 80,000 | good | good |
| Ex. 13 | M-1 | B-1 | D24 | A-1 | C-1 | 1 | DV-1 | 70,000 | good | good |
| Ex. 14 | M-2 | B-3 | D37 | A-3 | C-1 | 1 | DV-3 | 50,000 | good | good |
| Ex. 15 | M-2 | B-3 | D36 | A-4 | C-3 | 2.5 | DV-3 | 50,000 | good | good |
| Ex. 16 | M-2 | B-1 | D25 | A-2 | C-2 | 1.8 | DV-1 | 80,000 | good | good |
| Comp. Ex. B | M-1 | B-1 | — | A-2 | C-1 | 1.5 | DV-1 | image flow | image flow | good |

As is evident from Table 2, according to the lithographic printing plate of the present invention, an excellent lithographic printing plate can be provided under such a condition that plate making can be made with high productivity by scanning exposure, namely under a considerably low energy exposure condition. On the other hand, practically usable lithographic printing plate could not be obtained in Comparative Example 8 in which the initiation system of the present invention was not used.

Example 17

A lithographic printing plate precursor was prepared in the same manner as described in Examples 1 to 8, except that the initiation system was changed to the following composition, and the coat thickness of photopolymerization layer was changed to 1.5 g/m².

| Initiation system | D35 | 0.07 g |
|---|---|---|
| Titanocene | A-1 | 0.08 g |
| Co-sensitizer | C-2 | 0.2 g |

The thus obtained lithographic printing plate precursor was subjected to scanning exposure using a monochromatic light of 400 nm under such conditions that the exposure energy density became 0.25 mJ/cm². Next, the plate was heated at 100° C. for 10 seconds and then subjected to the aforementioned developing treatment.

A lithographic printing plate having blue image with excellent visibility was obtained. When offset printing was carried out using the thus obtained plate and a printing machine KOR-D manufactured by Heidelberger, it was able to obtain 50,000 sheets or more of prints having excellent image density and anti-scuimming property.

Example 18

The plate of Example 17 was exposed to a yellow light for 1 hour before the exposure and then the plate making and printing were carried out completely in the same manner. Completely the same good results of Example 17 were obtained.

Example 19

The plate of Example 18 was stored for 3 days under forced storing conditions of 65% humidity and 45° C. and then the plate making and printing were carried out in the same manner as the case of Example 17. Good results similar to those-of Example 17 were obtained.

Example 20

A photosensitive layer composed of the following composition was coated on a PET film to a coating amount of 2.0 g/m².

The content among photosensitive layer total components

| Binder resin (polymethyl methacrylate) | | 90 wt % |
|---|---|---|
| Sensitizing dye | D15 | 1.5 wt % |
| Activator | A-6 | 5.0 wt % |
| Acid-achromatic dye (naphthalenesulfonic acid salt of Victoria Pure Blue) | | 2.0 wt % |

The thus obtained blue sensitive material was subjected to 30 seconds of exposure using a metal halide lamp. The material was changed to a light yellow transparent film due to complete disappearance of the blue color.

Thus, this initiation system functions also as an acid generator.

Example 21

The procedure of Example 20 was repeated, except that the activator was changed to A-7. Photo-achromium of the dye was observed similar to the case of Example 20.

Example 22

The procedure of Example 21 was repeated, except that the activator was changed to A-8. Photo-achromium of the dye was observed.

Example 23

A photosensitive layer composed of the following composition was coated on a PET film to a coating amount of 2.0 g/m².

The content among photosensitive layer total components

| | | |
|---|---|---|
| Binder resin (polymethyl methacrylate) | | 90 wt % |
| Sensitizing dye | D26 | 1.5 wt % |
| Activator | A-9 | 8.5 wt % |

The coat film on the surface of the thus obtained photosensitive material showed a pH value of 5.6 when measured. Next, when the photosensitive material was subjected to 5 minutes of exposure using a xenon lamp and then its coat film pH was measured, it was found to be 9.5.

Thus, this initiation system has an optical base generating ability.

Example 24

A photosensitive layer composed of the following composition was coated on a PET film to a coating amount of 2.0 g/m².

The content among photosensitive layer total components

| | | |
|---|---|---|
| Binder resin (polymethyl methacrylate) | | 90 wt % |
| Sensitizing dye | D15 | 1.5 wt % |
| Activator | A-6 | 5.0 wt % |
| Oxidation coloring dye (Leuco Crystal Violet) | | 2.0 wt % |

The thus obtained light yellow transparent photosensitive material was subjected to 30 seconds of exposure using a metal halide lamp. It developed a bright blue color. This is considered to be oxidation coloring of the leuco pigment effected by the radical formation in this initiation system.

Structures of the compounds used in Examples and Comparative Examples, excluding the formulae 1 to 3, are as follows.

-continued

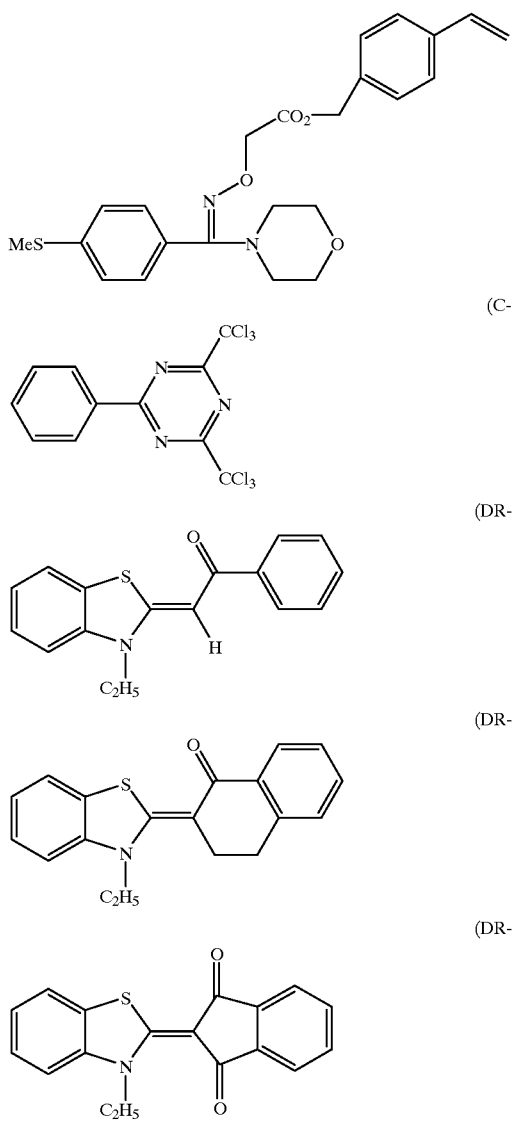

(In the above formulae, Ts means tosyl group.)

The lithographic printing plate precursor of the present invention can provide a lithographic printing plate which has sufficient sensitivity suited for the scanning exposure by a short wave semiconductor laser such as InGaN and is excellent in terms of printing durability, anti-scumming property and stability. Since the lithographic printing plate precursor for scanning exposure use of the present invention has markedly improved fogging under yellow light, workability for handling plates can be sharply improved. In addition, the photo-initiation system of the present invention has excellent sensitivity and can generate radicals, acids and bases.

What is claimed is:

1. A photosensitive composition which comprises (i) a sensitizing dye represented by formula (I), (ii) an activator compound that generates chemical changes by its interaction with an electronic excitation condition induced by light absorption of the sensitizing dye represented by the formula (I) and thereby produces at least one of radicals, acids and bases and (iii) a compound whose physical or chemical characteristics are changed and maintained by undergoing reaction with at least one of radicals, acids and bases;

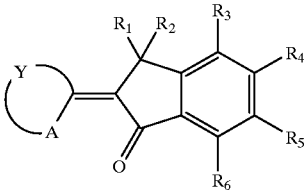

wherein A represents S atom or $NR_7$, Y represents a non-metallic atomic group which forms a nitrogen and/or sulfur-containing heterocyclic ring which does not contain a carbonyl carbon as a ring-constituting atom together with the adjacent A and carbon atom, each of $R_1$, $R_2$, $R_3$, $R_4$, $R_5$ and $R_6$ independently represents a monovalent, non-metallic group, and $R_7$ represents an alkyl group or an aryl group.

2. The photosensitive composition according to claim 1, wherein the compound whose physical or chemical characteristics are changed and maintained by undergoing reaction with at least one of radicals, acids and bases is an addition-polymerizable compound having an ethylenic unsaturated double bond.

3. The photosensitive composition according to claim 1, wherein the nitrogen and/or sulfur-containing heterocyclic ring which does not contain a carbonyl carbon as the ring-constituting atom represented by Y is selected from the group consisting of thiazoles, oxazoles, selenazoles, thiazolines, quinolines, imidazoles, indolenines, pyridines and dithiols.

4. A 1,3-dihydro-1-oxo-2H-indene derivative represented by formula (II);

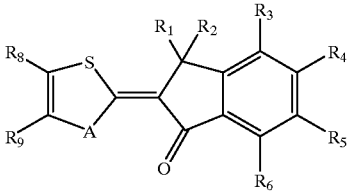

wherein A represents S atom or $NR_7$, each of $R_1$, $R_2$, $R_3$, $R_4$, $R_5$, $R_6$, $R_8$ and $R_9$ independently represents a monovalent non-metallic atomic group, and $R_7$ represents an alkyl group or an aryl group, wherein $R_8$ and $R_9$ are separate groups or combine with each other to form a five- to eight-membered ring.

5. A photopolymerization initiation system which comprises a sensitizing dye represented by formula (II) of claim 4 and an activator compound that generates chemical changes by its interaction with an electronic excitation condition induced by light absorption of the sensitizing dye represented by the formula (II) and thereby produces at least one of radicals, acids and bases.

6. A photopolymerization composition which comprises a sensitizing dye represented by formula (II) of claim 4, an activator compound that generates chemical changes by its interaction with an electronic excitation condition induced by light absorption of the sensitizing dye represented by the formula (II) and thereby produces at least one of radicals, acids and bases, and a compound whose physical or chemical characteristics are changed and maintained by undergoing reaction with at least one of radicals, acids and bases.

* * * * *